(12) United States Patent
Wilson et al.

(10) Patent No.: US 8,146,599 B2
(45) Date of Patent: Apr. 3, 2012

(54) PATIENT POSITIONING SYSTEM

(75) Inventors: Roger F. Wilson, Sarasota, FL (US); Marc Mlyn, Port Jefferson Station, NY (US); Leo G. de Mooy, PD Gouda (NL); Geoffrey Dalbow, Eagle, CO (US); Willet F. Whitmore, III, Longboat Key, FL (US); Bruce Ribble, Swisher, IA (US)

(73) Assignee: CIVCO Medical Instruments Co., Inc., Kalona, IA (US)

( * ) Notice: Subject to any disclaimer, the term of this patent is extended or adjusted under 35 U.S.C. 154(b) by 302 days.

(21) Appl. No.: 12/431,121

(22) Filed: Apr. 28, 2009

(65) Prior Publication Data

US 2009/0308400 A1 Dec. 17, 2009

Related U.S. Application Data

(60) Provisional application No. 61/073,174, filed on Jun. 17, 2008.

(51) Int. Cl.
*A61G 15/00* (2006.01)
*A61F 5/37* (2006.01)
*A47B 7/00* (2006.01)

(52) U.S. Cl. .............................. 128/845; 128/870; 5/621
(58) Field of Classification Search .................. 128/845, 128/870; 5/601, 621, 624, 622, 640, 647–648, 5/650; 600/415, 417, 421; 378/209
See application file for complete search history.

(56) References Cited

U.S. PATENT DOCUMENTS

| 3,840,221 A * | 10/1974 | Hogan ............................... 5/601 |
| 5,454,993 A * | 10/1995 | Kostich ......................... 264/46.4 |
| 5,832,550 A * | 11/1998 | Hauger et al. ..................... 5/621 |
| 6,161,237 A | 12/2000 | Tang et al. |
| 6,622,324 B2 * | 9/2003 | VanSteenburg et al. .......... 5/621 |

FOREIGN PATENT DOCUMENTS

| EP | 1366714 A2 | 3/2003 |
| WO | 0143592 A1 | 6/2001 |
| WO | 2006081412 A2 | 8/2006 |
| WO | WO 2006081412 A2 * | 8/2006 |

OTHER PUBLICATIONS

International Search Report for Application No. PCT/US2009/047154 dated Oct. 7, 2009.

* cited by examiner

*Primary Examiner* — Patricia Bianco
*Assistant Examiner* — Kari Petrik
(74) *Attorney, Agent, or Firm* — Caesar, Rivise, Bernstein, Cohen & Pokotilow, Ltd.

(57) ABSTRACT

A system for positioning a patient on a treatment couchtop for SBRT is provided. The system includes a patient support panel and at least one positioning/fixation component for releasable mounting on the patient support panel at a desired position to immobilize a portion of the patient's body. The patient support panel includes a pair of longitudinally extending side rails having a series of longitudinally spaced indexing apertures for receipt of a locking bar for mounting a positioning/fixation component thereon at a discrete index position. The at least one positioning component includes a pair of clamping mechanisms for releasably securing that component to the side rails at any longitudinal position along the side rails.

20 Claims, 20 Drawing Sheets

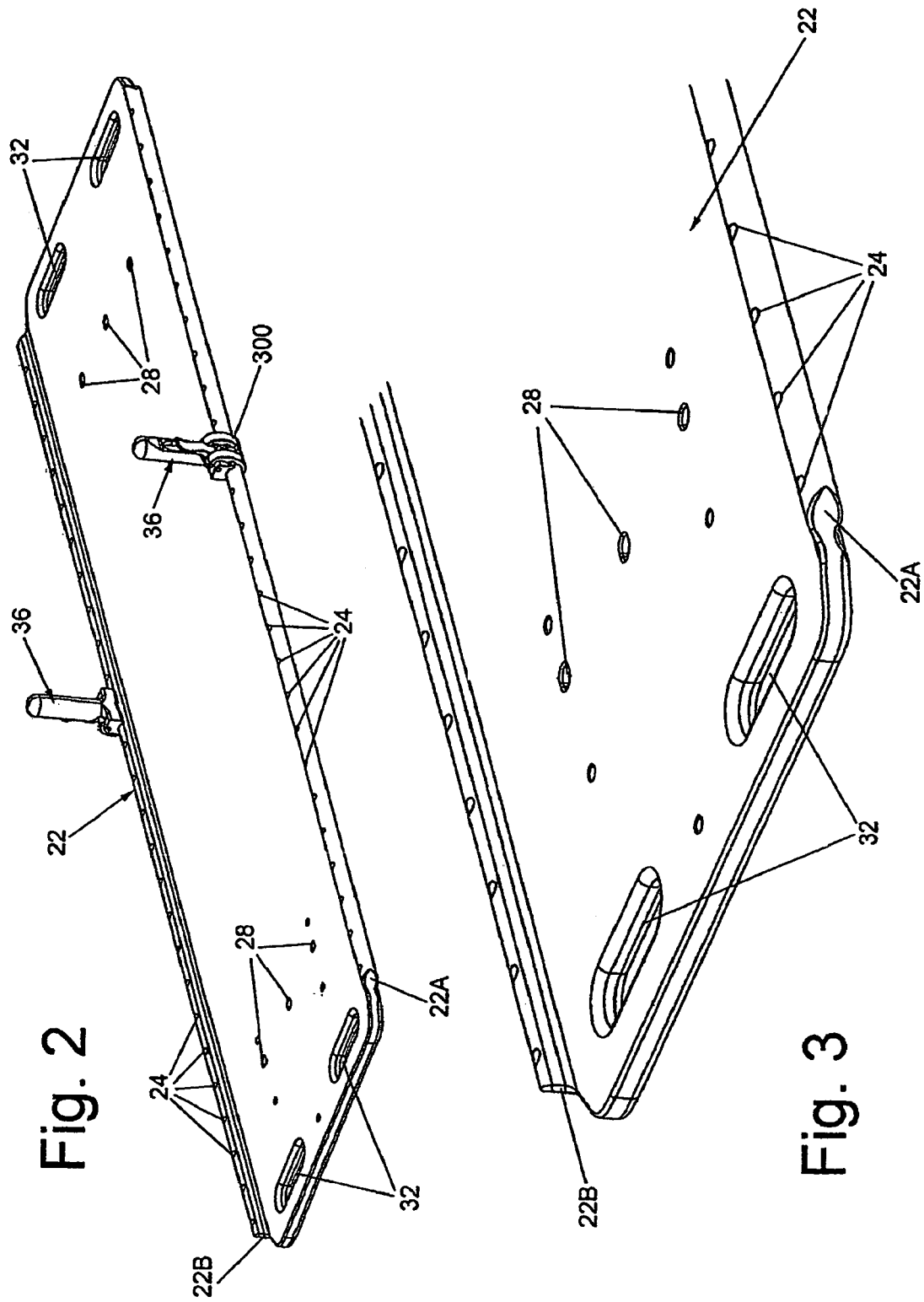

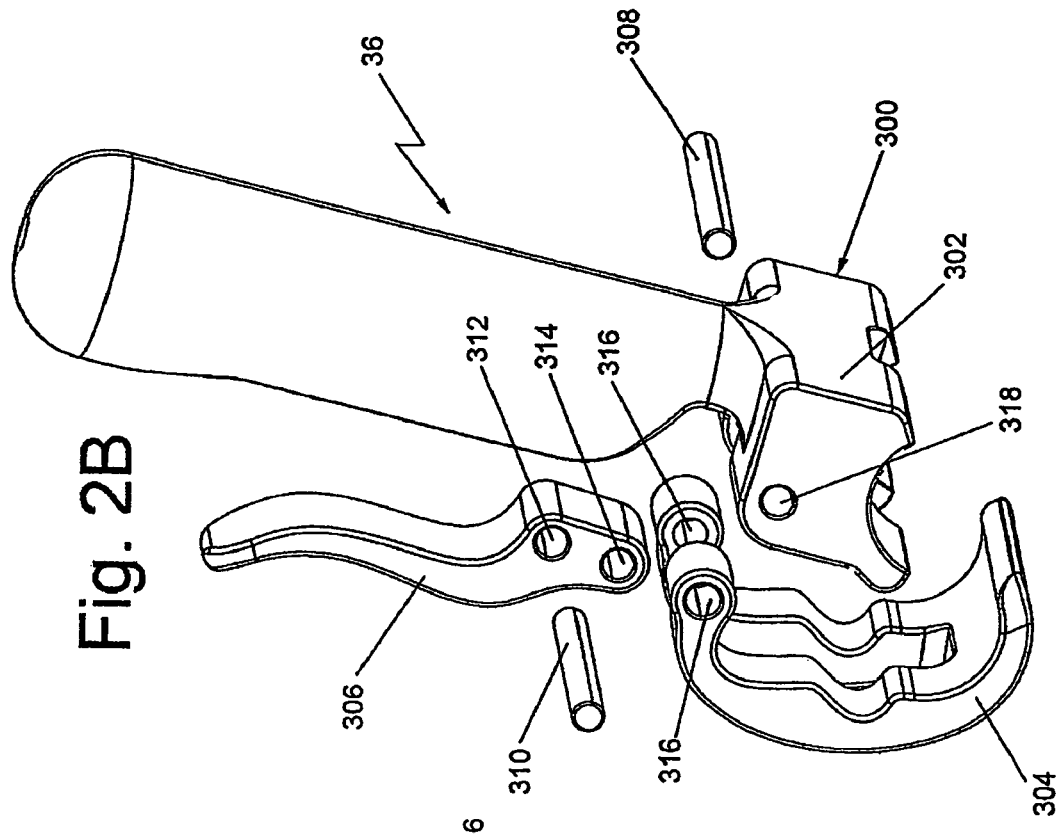
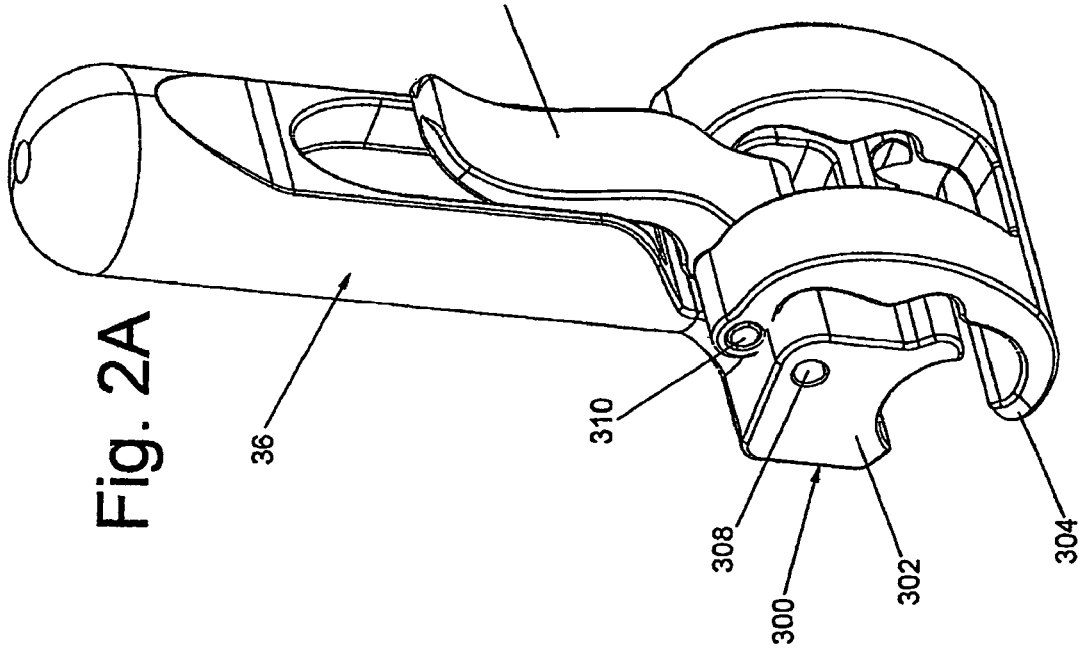

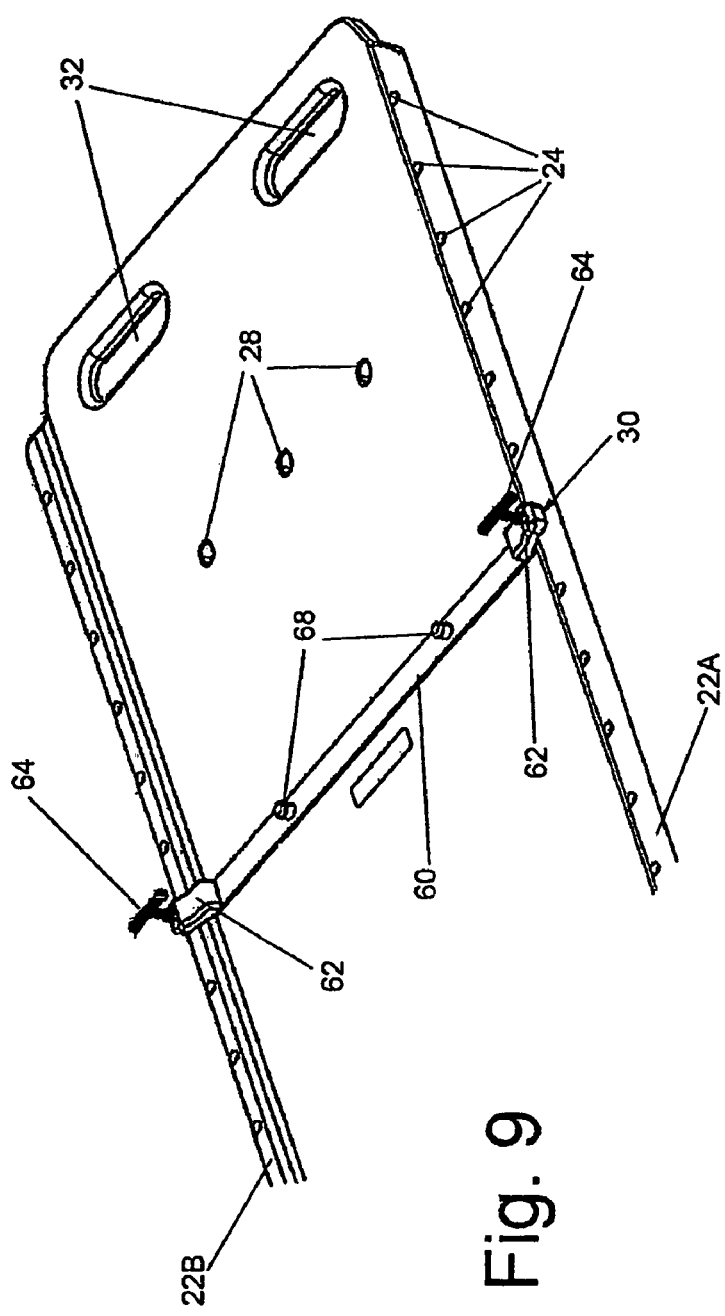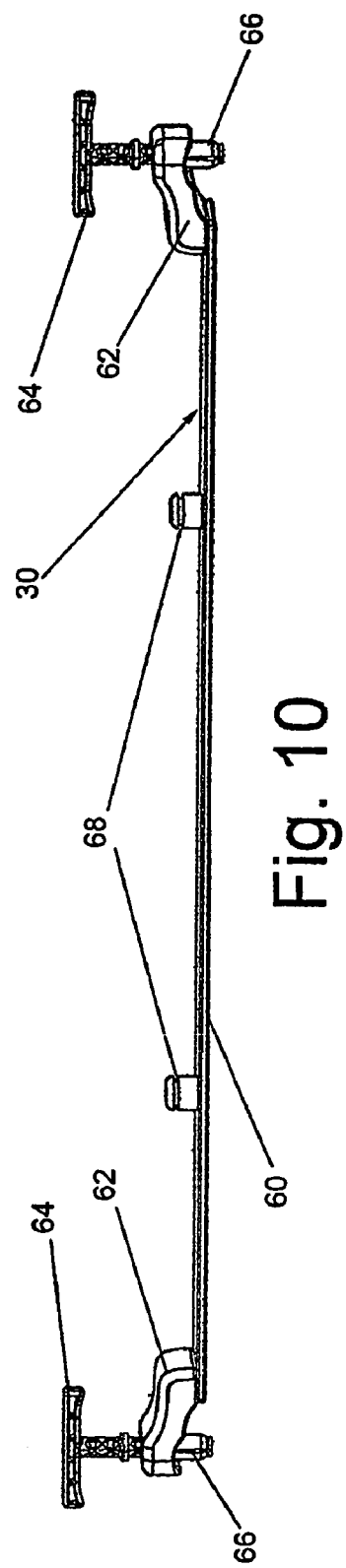

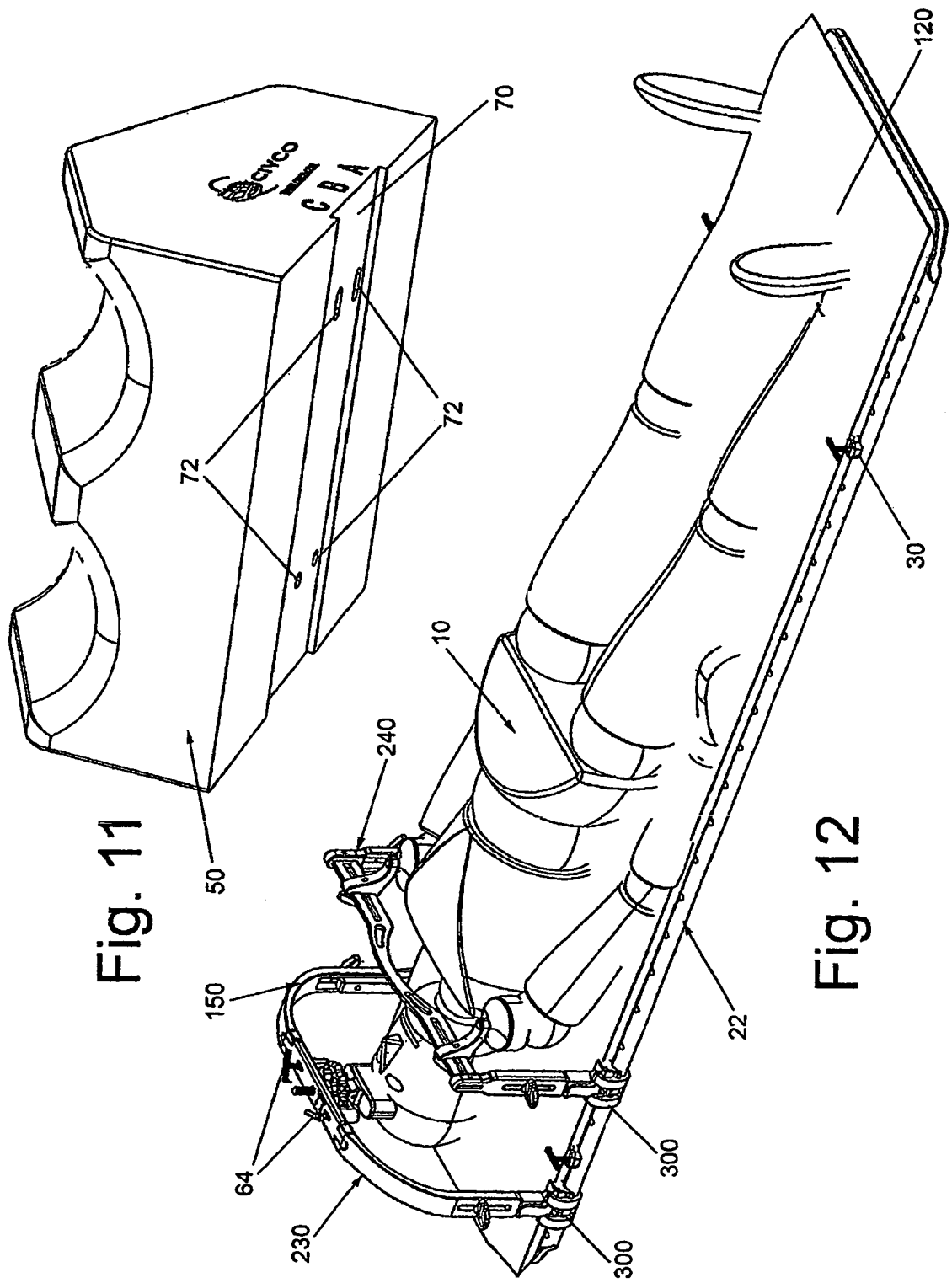

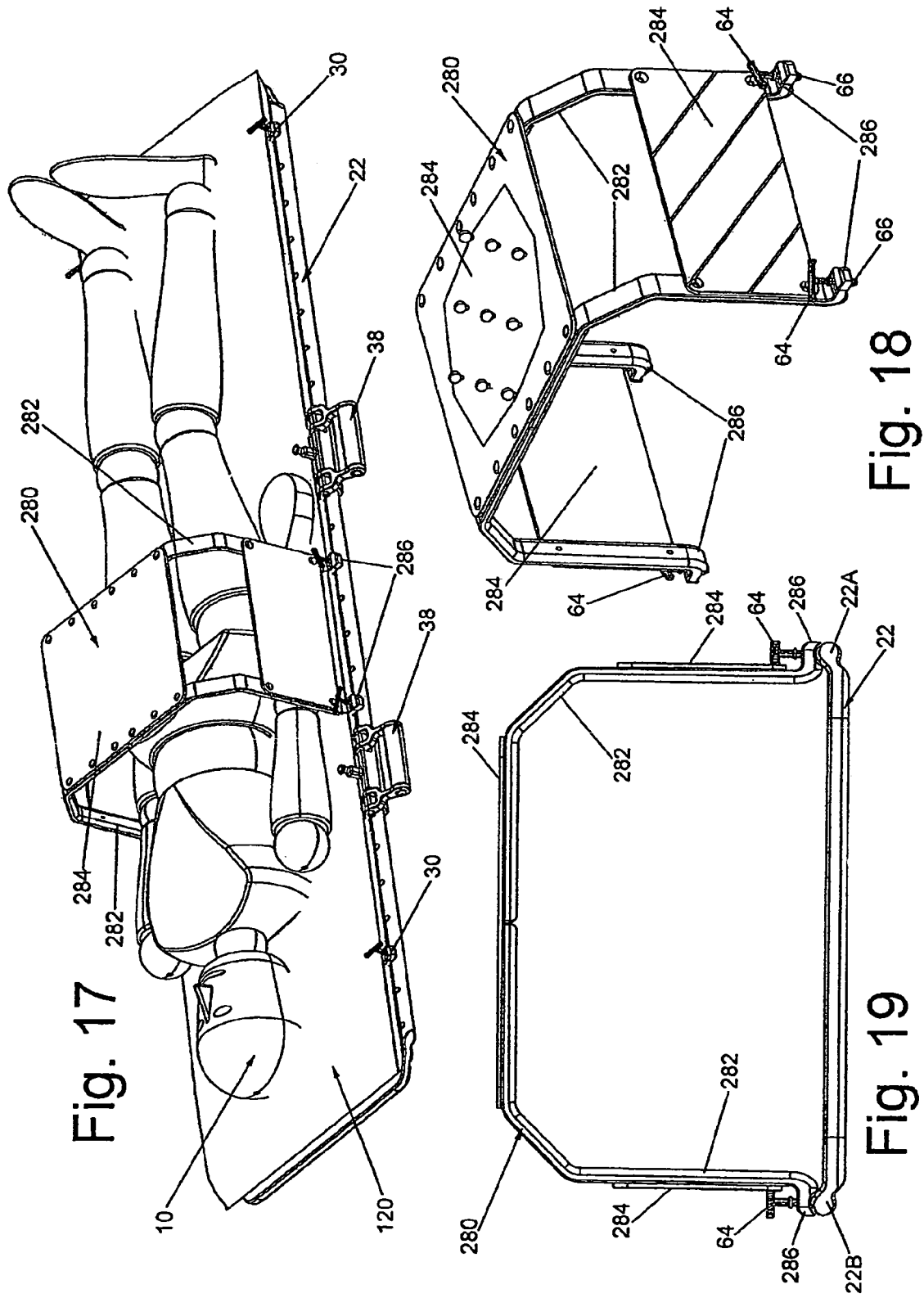

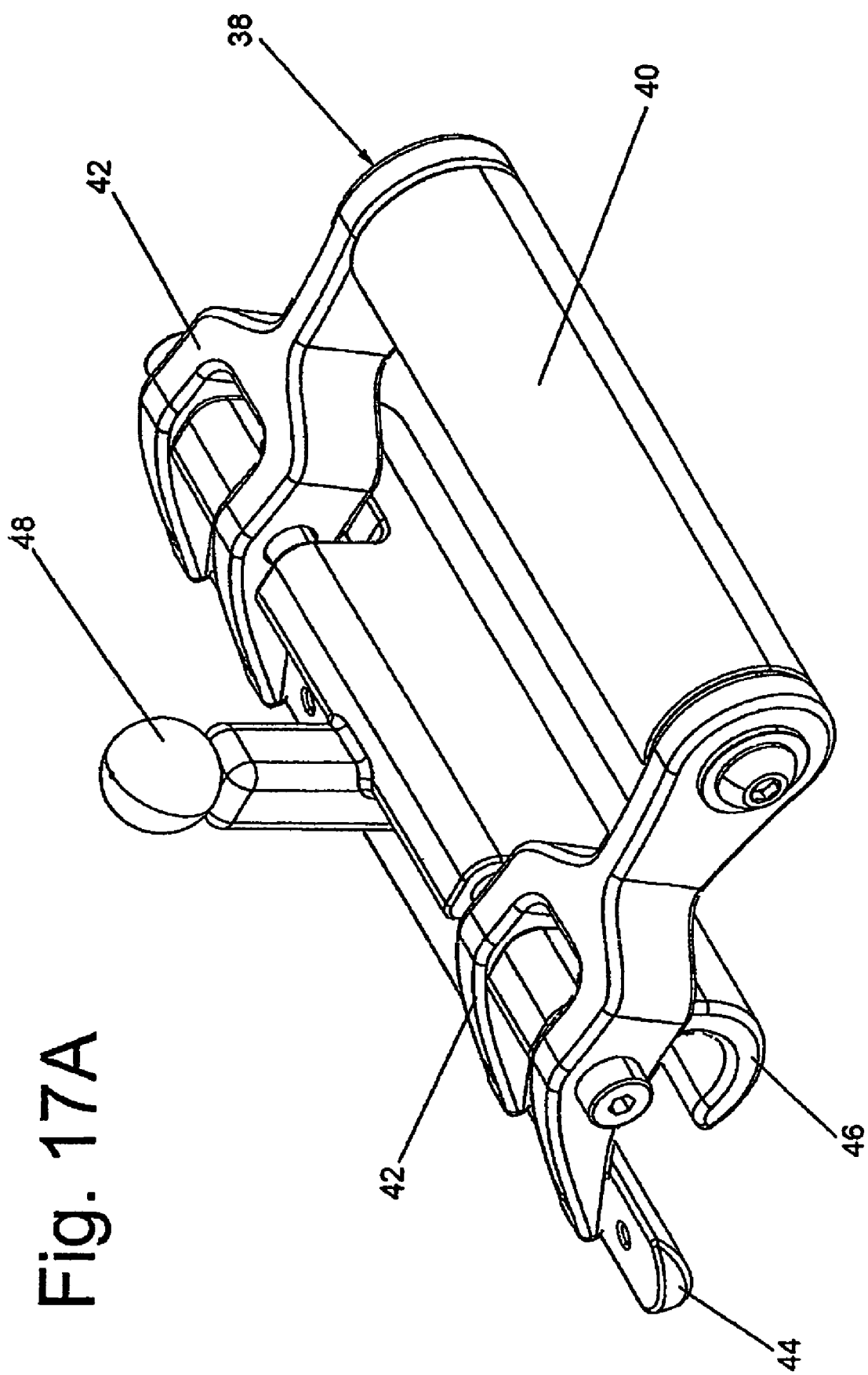

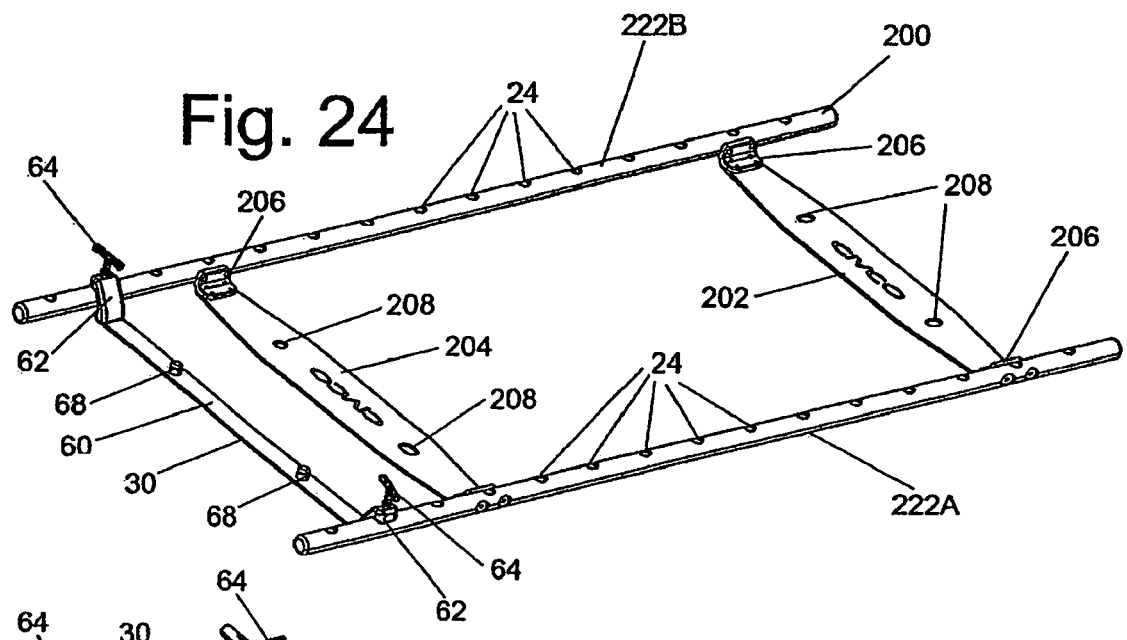
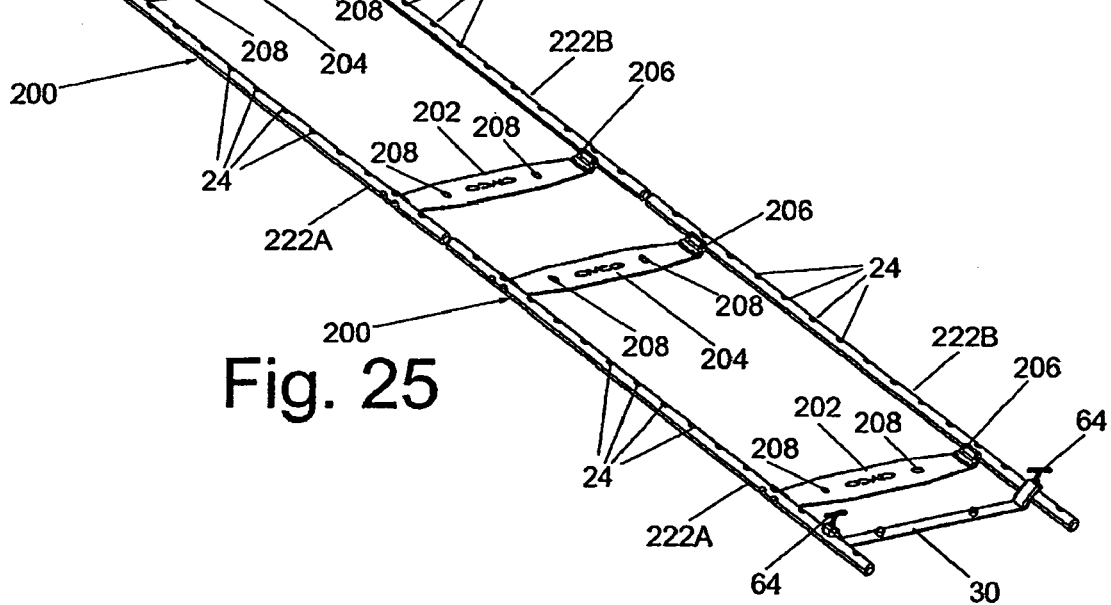

PATIENT POSITIONING SYSTEM

CROSS-REFERENCE TO RELATED APPLICATIONS

This application claims priority from Provisional Application Ser. No. 61/073,174, filed on Jun. 17, 2008, entitled Patient Positioning System For Stereotactic Radiation Therapy, which application is assigned to the same assignee as this application and whose disclosure is incorporated by reference herein.

STATEMENT REGARDING FEDERALLY SPONSORED RESEARCH OR DEVELOPMENT

"Not Applicable"

INCORPORATION-BY-REFERENCE OF MATERIAL SUBMITTED ON A COMPACT DISK

"Not Applicable"

FIELD OF THE INVENTION

This invention relates generally to holding devices and more particularly for systems for holding positioning, fixation and associated devices on a radiation treatment couch or other patient support structure.

BACKGROUND OF THE INVENTION

As will be appreciated by those skilled in the art, radiation therapy treatment for extracranial malignancy is trending toward fewer radiation fractions and higher doses per fraction over shorter periods of time. This is occurring because of theoretical advantages in the effect on tumor biology and both economic and social advantages related to a shorter treatment period and fewer trips to the clinic. This modality has been enabled by tremendous improvements in imaging with better tumor definition and visualization of surrounding structures combined with advances in linear accelerator (LINAC) beam targeting and dose painting technologies. The devices and methods of treatment required to accomplish this are collectively referred to as stereotactic body radiotherapy (SBRT). Previously, stereotactic radiotherapy has been applied mainly to brain tumors and often has been reduced to a single, high dose, precisely targeted treatment using an external frame that is bolted to the skull, so called stereotactic radiosurgery (SRS). Stereotaxy may be defined as the three dimensional spatial localization targeting of an object by using its known measured relationship to an adjacent set of objects. The objects in known relative position may be located in an external frame that is fixed in relation to the tumor as has historically been done for SRS, or may be any set of reference points having a known physical relationship to the target that may be available, so called "frameless stereotaxy".

SBRT is a new and rapidly developing area of cancer management. Consequently, the devices and methods that support it are not yet optimized or widely shared, and many different paths have been taken.

Patient positioning is a prime example. Some investigators feel that extremely precise and reproducible patient positioning is critical, whereas others believe that frequent re-localization of the target with imaging is more important. Some centers have invested in robotic LINACS that will move the beam to track a moving target, whereas others have invested in patient positioning and immobilization systems that restrict movement of the target tumor by restricting respiratory movement of the chest wall and/or diaphragm. Several device manufacturers have developed individual solutions for one camp or another. All parties are in agreement that keeping the patient as still as possible when the treatment beam is on, within some boundaries of comfort and the physiological processes that are required to sustain life, is highly desirable.

Patients undergoing SBRT typically are disposed on a treatment couch or table associated with LINAC or other the radiation therapy apparatus. Various couchtops and overlays are commercially available for disposition on the treatment couch, with the patient being disposed on the couchtop/overlay. As is known an overlay is disposed on top of the cradle, existing support frame and/or spine of a CT, simulator or LINAC. For SBRT applications it is a common practice to position and fix a portion of the patient so that repeated treatment can be given to the patient. To that end, some indexing system is provided for mounting and positioning various patient positioning and/or fixation devices on the couchtop or overlay at predetermined positions with respect to the couchtop/overlay. Examples of such patient positioning/fixation devices are head and neck positioning/fixation devices, breast and thorax positioning/fixation devices, and hip and pelvic region positioning/fixation devices. Many of such devices, as well as other miscellaneous positioning aids, e.g., cushions, wedges, etc., for use on the treatment couchtop/overlay are available from the assignee of this invention, Civco Medical Solutions (hereinafter "CIVCO"), and are shown in its "Radiation Oncology Sourcebook"© 2007.

The treatment couchtops/overlays available from CIVCO make use of an array of equidistantly spaced indexing points running down the side of the couchtop/overlay. A two-pin LOK-BAR™ also sold by CIVCO is arranged to be connected to the couchtop overlay at any of the indexing points. The two-pin LOK-BAR™ is an elongated bar that includes two pins projecting upward from it to interface (be received in) corresponding holes on CIVCO's line of patient positioning and fixation devices. To index a particular positioning/fixation device to the couchtop or overlay the LOK-BAR™ is attached to the couchtop or overlay via any of the multiple indexing points. The particular patient positioning/fixation device is then mounted on the LOK-BAR™ by disposing it on the LOK-BAR™ so that the two-pins of the LOK-BAR™ are received within corresponding apertures in the positioning/fixation device. By indexing the patient positioning/fixation device(s) to the same indexing points for every radiation treatment one can be assured of increased target accuracy and patient throughput.

Other manufacturers also provide couchtops/overlays with indexing systems and positioning/fixation devices to be used with such indexing systems. While there are devices that are commercially available to perform a specific method of patient positioning and/or immobilization and there are specific devices designed for various niche approaches to SBRT, what is missing is a general solution for immobilizing patients that is sufficiently versatile to have broad appeal to multiple centers doing SBRT. In short, what is needed is an integrated solution that allows the user to tailor the positioning and immobilization methods to suit the patient, their LINAC (or other therapy apparatus) and their treatment plan.

The present invention addresses that need by providing a system for reproducible patient positioning and immobilization during SBRT. In particular, the system makes use of a modular design that allows a broad range of established positioning and immobilization techniques to be applied as needed. Patient comfort, setup time and patient transportation are optimized. The system basically comprises a portable platform (referred to as a patient support panel) having a pair of rails that enable full indexing of various components used during SBRT along its length. Those components also form part of the subject system and include modular multifunctional bridges and other positioning/fixation components and other components/accessories that may be positioned anywhere along the length of the platform to be used to position/fix the patient or provide any other function desired during SBRT treatment. The multifunctional bridges are particularly significant in that they can be positioned where needed to provide various types of immobilization, hold instrumentation or enable stereotactic frames or other positioning and localization devices to be used.

Those bridges, the patient support panel and the other modular accessories/component of the subject invention will be described in detail later. Suffice it for now to state that they allow the user to apply any of the full range of positioning and immobilization techniques that are in current use for SBRT. And, this is accomplished with the likelihood of greater comfort for the patient and ease of use for the therapist. The patient support panel accommodates standard stereotactic frames or frameless approaches to treatment. In addition, the patient support panel is designed to be transportable with the patient immobilized on it. Thus, workflow may be improved by allowing time consuming patient setup to be completed outside the expensive LINAC room and then have the SBRT platform precisely positioned on the standard LINAC treatment couch. Alternatively, the patient support panel with the patient immobilized on it could be transferred to an imaging device such as a CT or MR scanner to update targeting data prior to therapy and then be transferred to the LINAC couch without movement of the patient in relation to the platform.

All references cited and/or identified herein are specifically incorporated by reference herein.

SUMMARY OF THE INVENTION

In accordance with one aspect of the invention there is provided a system for positioning a patient on a treatment table, e.g., a LINAC couchtop, for some type of therapy that is to be repeated, e.g., SBRT, wherein the position of at least a portion of the patient's body to be treated is to be held in a predetermined fixed position, The system comprises a patient support panel and at least one positioning component, e.g., a bridge member, arranged to be releasably mounted on the patient support panel at a desired position thereon to hold the at least one portion of the patient's body at the desired position. The patient support panel comprises a generally planar member having a pair of longitudinally extending side rails. Each of the side rails has a series of longitudinally spaced indexing apertures. The apertures are aligned in pairs for releasably mounting a first component, e.g., a cushion for supporting and holding the portion of the patient's body thereon, between any of the pairs at a desired longitudinal position along the patient support panel via a component mounting bar having at least one pin projecting upward therefrom for receipt within the first component. The at least one positioning component includes at least one clamp for releasable securement to a respective one of the side rails at any longitudinal position along the side rail.

In accordance with another aspect of this invention there is provided a device for use on a patient treatment table to enable some type of therapy that is to be repeated to be provided to a patient, wherein the position of at least a portion of the patient's body to be treated is to be held in a predetermined fixed position. The device basically comprising a frame arranged to be mounted on the treatment table. The frame includes a pair of longitudinally extending side rails, each of which has a series of longitudinally spaced indexing apertures. The apertures are aligned in pairs for releasably mounting a first component between any of the pairs of apertures at a desired longitudinal position along the device via a component mounting bar having a pair of pins projecting upward therefrom for receipt within the first component. The side rails are also arranged to releasably mount at least one positioning component thereon at any longitudinal position along the side rails by means of at least one clamping member associated with the at least one positioning component.

In accordance with still another aspect of this invention a system for positioning a patient on a table for an MRI imaging procedure is provided. That system comprises a patient support panel, a positioning component, and an MRI coil device. The positioning component is arranged to be releasably mounted on the patient support panel at a desired position with respect to the patient's body and is in the form of a bridge member comprising a pair of upstanding legs and a central section bridging the legs. The MRI coil device is arranged to be releasably mounted on the bridge member. Each of the legs of the bridge member includes a lower end having a connector arranged for releasable securement to a portion of the patient support panel at various longitudinal positions along the patient support panel. Each of the legs of the bridge member is adjustable in height with respect to the central section of the bridge member so that the MRI coil and frame member can be positioned and held close to a desired portion on the body of the patient.

DESCRIPTION OF THE DRAWING

FIG. 2 is an isometric view of the patient support panel of constructed in accordance with this invention shown with two patient positioning handles also constructed in accordance with this invention;

FIG. 2A is an enlarged isometric view of one of the two handles shown in FIG. 2;

FIG. 2B is an exploded isometric view of the components making up the handle shown in FIG. 2A;

FIG. 3 is an enlarged isometric view of a portion of the patient support panel shown in FIGS. 1 and 2;

FIG. 9 is an isometric view of a portion of the patient support panel and the locking bar shown in FIG. 8, but without the leg positioning cushion;

FIG. 10 is an enlarged front elevation view of the locking bar shown in FIG. 9;

FIG. 11 is an enlarged isometric view of the leg positioning cushion shown in FIGS. 1 and 8;

FIG. 12 is an isometric view of another exemplary embodiment of a system constructed in accordance with this invention for positioning/fixing the head and shoulders a patient on conventional radiation therapy table or couch for stereotactic radiation therapy or any other treatment requiring repeated immobilization of the particular portion(s) of patient's body;

FIG. 17 is an isometric view of still another exemplary embodiment of a system constructed in accordance with this invention showing a patient on the patient support panel with a fiducial targeting frame constructed in accordance with this invention and with plural handles also constructed in accordance with this invention for lifting the entire assembly to place it on a conventional radiation therapy table or couch;

FIG. 17A is an enlarged isometric view of each of the handles shown in FIG. 17;

FIG. 18 is an isometric view of the stereotactic fiducial frame shown in FIG. 17;

FIG. 19 is a front elevation view of the fiducial frame shown in FIG. 18;

FIG. 24 is an isometric view of a half rail frame constructed in accordance with this invention arranged to be directly mounted to any conventional couchtop via a conventional two pin lock bar registration system to enable the various modular positioning/fixing components and accessories of this invention to be mounted thereon;

FIG. 25 is an isometric view of two half sections like shown in FIG. 24 connected together to form a full frame section in accordance with another embodiment of the system of this invention;

DETAILED DESCRIPTION OF THE PREFERRED EMBODIMENT

Figure 1:
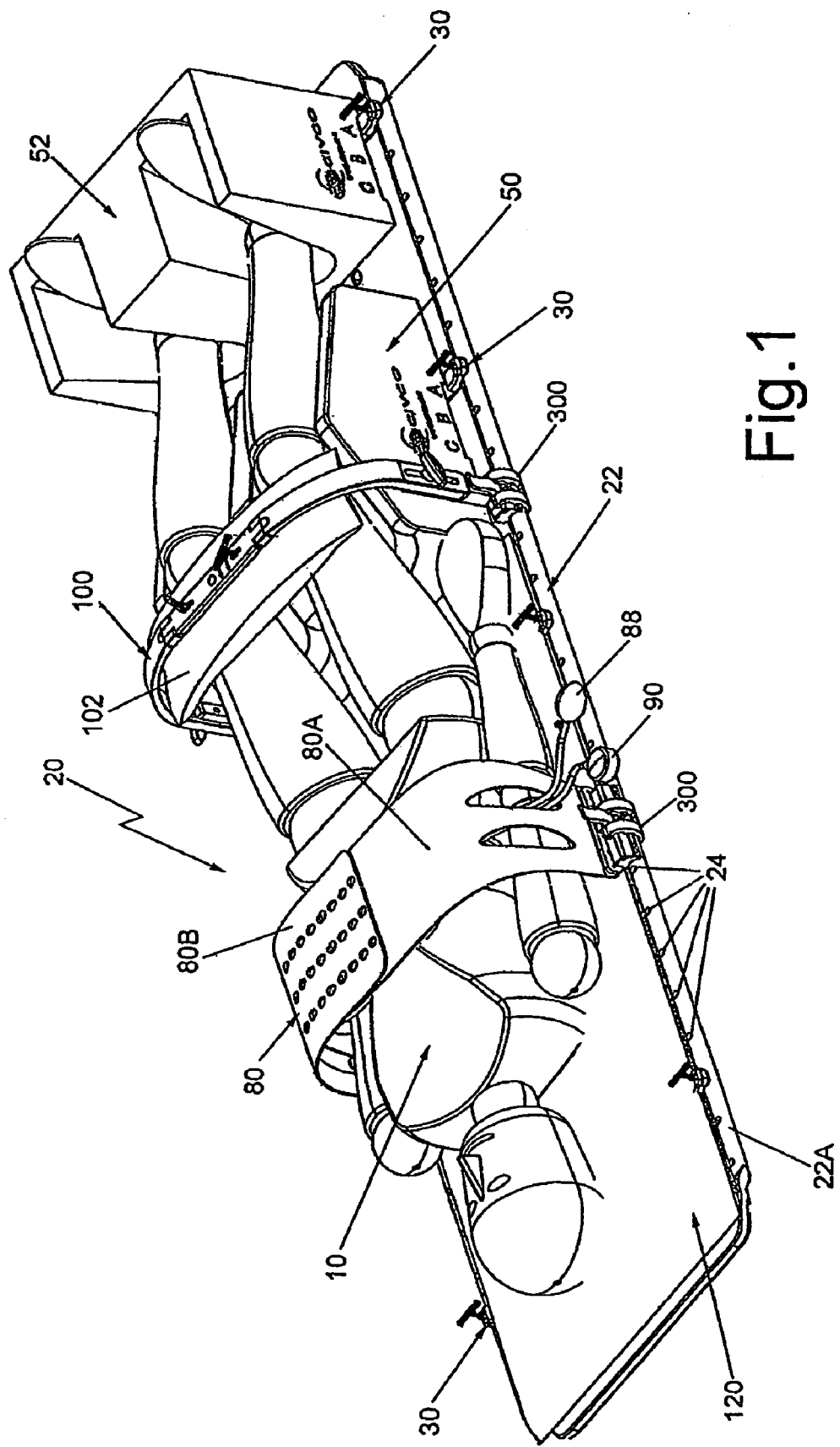
FIG. 1 is an isometric view of one exemplary embodiment of the system constructed in accordance with this invention showing a patient support panel and four exemplary positioning/fixation devices mounted thereon to position/fix the upper abdomen and legs of a patient's body for stereotactic radiation therapy or any other treatment requiring repeated immobilization of the particular portion(s) of patient's body.

Referring now to the various figures of the drawing wherein like reference characters refer to like parts, there is shown in FIG. 1 a system 20 for use on a convention LINAC couchtop or table (not shown) to repeatedly position/fix any portion of the body of a patient 10 at any desired position(s) for SBRT or any other procedure requiring repeated immobilization of that portion(s) of patient's body. The system 20 basically comprises a patient support panel 22, and a plurality of modular components (to be described later) that are arranged to be releasably mounted on the patient support panel. For example, in the exemplary embodiment of FIG. 1 the modular components are a pneumatically operated respiratory restriction device 80, a bridge-supported leg restriction device 100, a conventional knee support cushion 50, a conventional foot support cushion 52 and a conventional torso support cushion or pad 120. Those components are merely exemplary of a myriad of components, conventional and otherwise (several of which will be specifically described herein), that can be mounted on the patient support panel for repeated use in SBRT.

It should be pointed out at this juncture that the patient support panel 22 of the system of this invention is also particularly suited for use in an invention disclosed in a United States Provisional patent application filed contemporaneously herewith entitled "Patient Transfer System For Use In Stereotactic Radiation Therapy", which is assigned to the same assignee as this invention and whose disclosure is specifically incorporated by reference herein. That system will be referred to hereinafter as the "PTS" or "Patient Transfer System" and basically comprises at least one low friction transfer plate disposed on the gurney and at least one similar low friction transfer plate disposed on the treatment couchtop. A plurality of bridging members are provided between the transfer plates to bridge the gap between the gurney and the treatment couchtop to facilitate the sliding of the patient support panel with the patient thereon from the gurney to the treatment couchtop and vice versa.

As best seen in FIGS. 2, 3 and 9 the patient support panel basically comprises a generally planar member which is of sufficient size to support an adult patient 10 in a prone position like shown in FIGS. 1, 12 and 17. In one preferred embodiment the patient support panel or platform is formed of a foam sandwich composite, e.g., FRP carbon or aramid fibers (e.g., KEVLAR®), but can be formed of other strong non-metallic materials, such as fiberglass. The patient support panel 22 and has a pair of longitudinally extending rails 22A and 22B that enable full indexing of various components used during SBRT along its length. In particular, the longitudinal side edges of the patient support panel are of a bulbous form in cross section to define the rails 22A and 22B. A plurality of equidistantly spaced (i.e., 7 cm), indexing apertures or holes 24 are provided along the length of each rail. The apertures 24 are aligned transversely in pairs so that a two-pin registration or locking bar 30 (FIGS. 9 and 10) can be mounted on the patient support panel 22 between any pair of apertures 24. The two-pin locking bar 30 will be described in detail later. Suffice it for now to state that it constitutes a modification of the universally accepted multi-pin registration system. In particular, all standard/generic treatment couchtops, such as those available from Medtec, Sinmed, Varian Medical Systems, Inc., Elekta Ala., and others use a pin system to attach positioning and immobilizing (fixation) devices or other components, e.g., vacuum bags, knee rests, foot supports, head supports, etc., to the couchtop. Those positioning/fixation components are available from a number of vendors including CIVCO. The pin systems are in the form of a flat metal strip or bar (sometimes referred to a lock or locking bar) having registration pins, e.g., two pins (standard) or three pins (MR compatible), projecting upward to mount the positioning/fixation component thereon. The lock bar is arranged to be mounted on the couchtop and fixed to its surface at a desired indexed position by means (e.g., balls, sockets or clamps) mounted at the ends of the bar and which are arranged to engage cooperating means located at discrete index position on the couchtop.

The locking bar 30 of this invention includes releasably securable members, e.g., expandable push pins (to be described later), to render it particularly suited for releasable mounting on the patient support panel 22 via any of the index positions established by the aligned pairs of apertures 24. Thus, by using a locking bar 30 one can readily mount and position any positioning/fixation component or any other accessory or component on the patient support panel at any of the discrete index positions therealong.

One of the significant features of the system 20 of this invention is that various positioning/fixation components and/or other accessories that are to be mounted with the patient on the treatment couchtop include clamping mechanisms (to be described later) which enable them to be repeatedly positioned at any longitudinal position along the patient support panel and not merely at the discrete indexing points established by the pairs of apertures 24. Thus, positioning/fixation components and/or accessories can be mounted at any of the discrete index positions via the locking bars 30, and/or at any longitudinal position along the patient support panel via the clamping mechanisms of such components (to be described later). To facilitate repeatable mounting of those components on the rails 22A and 22B indexing indicia (not shown) are provided along the length of those rails.

As should be appreciated by those skilled in the art from the discussion to follow the patient support panel 22 enables one to readily set up the patient outside the treatment room and then transport him/her in treatment position to the treatment couchtop. Alternatively, if it is necessary to image the patient in a CT scanner in treatment position and transport him/her to the treatment room in the same position, the patient support panel provides a viable means to accomplish that end. It can also be used simply by placement on the treatment couch prior to patient setup. In either case this does result in a "double layer" of supporting tops, but that is of minor concern.

In FIGS. 24 and 25 there is shown a rail frame system 200 which will be described in detail later. Suffice it for now to state that the rail frame 200 can be used on a conventional couchtop to eliminate the use of the patient support panel 22 to hold the various components of the system 20 on the couchtop. Thus, the system 200 enables one to effectively retrofit existing treatment couchtops to be able to make use of the modular positioning/fixing components of this system. If the patient support panel 22 is to be used, e.g., it will be used to transport the patient and the associated positioning/fixing components in a set-up state to the treatment couchtop it can be mounted and indexed on the couchtop using the two pin or three pin lock bar systems. To that end, as can be seen in FIGS. 2 and 3 the patient support panel has two groups of holes or apertures 28, the outer two apertures being arranged to accept the two pins of a two pin lock bar system, while all three apertures are arranged to accept the three pins of a three pin lock bar system.

As mentioned above, the rails of the patient support panel 22 (or the rails of the rail frames 200 to be described with reference to FIGS. 24 and 25) include side rails having indexing or receiving holes every 7 cm for the two pin (or three pin) systems so that lock bars may be positioned and re-positioned exactly the same as on any generic treatment couchtop. The spacing between the indexing holes 24 is thus one half of the spacing provided by conventional treatment couchtops to provide a finer degree of longitudinal position adjustability.

Although not shown in the drawings, the patient support panel 22 has a slight recess on its underside that provides clearance for the bar that fixes the pins on the two pin or 3 pin locating lock bars. This underside recess allows the patient support panel to sit flush on a standard couchtop surface. The patient support panel 22 also includes four cut-outs, each forming a respective hand-hold 32 for transporting the patient support panel. The hand-holds 32 are disposed in pairs, located adjacent respective ends of the patient support panel.

For some applications it may be desirable to provide a pair of handles for the patient lying on the patient support panel to grasp. To that end, the system 20 includes a pair of patient handles 36 (FIG. 2), each of which is arranged to be releasably secured to a respective side rail 22A and 22B of the patient support panel at any longitudinal position there along. In order to accomplish that end, each handle includes a clamping mechanism for releasable securement to the respective side rails. Various types of clamping mechanisms can be used with this invention. One type constitutes an over-center levered latch mechanism and is shown in FIGS. 2, 2A and 2B. Another type constitutes a cam tensioner clamping mechanism and is shown best in FIGS. 22 and 23. The details of those two clamp mechanisms will be described later, suffice it for now to state that each includes a pair of jaws which are arranged to open with respect to each other to receive the periphery of a respective side rail 22A and 22B therebetween so that the clamp mechanism can be slid to any longitudinal position along that rail. Each of the jaws has a concave surface complementary to the profile of the rails 22A and 22B. Thus, once in the desired position the jaws can be closed to releasably secure the clamp mechanism at that longitudinal position.

The system for transporting the patient support panel 22 from gurney to treatment couchtop and from CT or MR scanner to gurney add to the value of patient support panel since it allows the time consuming step of accurate patient setup to be completed outside the treatment room or vault. High resolution imaging may be done for example in a standard CT scanner and with the patient "locked" into a known position using the various cushions, vacuum bags, bridges, etc. Then the patient can be smoothly transferred to the gurney and then to the treatment table saving a lot of valuable setup and imaging time in the treatment room. The transfer system for accomplishing that end is the heretofore identified Patient Transfer System and is simple, safe, smooth and accurate that relies on low friction, approximately level surfaces to work. Although low friction sliding surfaces are used in hospitals every day to transfer patients, the construction of the Patient Transfer System is unique in the use of the patient support panel beneath the patient, the method and components used to bridge the gaps between gurneys/tables on which the patient resides, and the methods and components used to accurately control the final position of the patient support panel, among other features.

The Patient Transfer System also uses the two pin (or three pin) locking bars to locate transfer plates of that system on the treatment or imaging surfaces, while doing that in turn allows precise positioning of the patient support panel on those surfaces. The transfer plates prevent damage to the undersurface of the patient support panel that would otherwise be caused by the protruding pin system when sliding the patient support panel into position. At the same time it allows the use of the highly accurate, universal two or three pin locating systems, and keeps the transfer plates applicable to all standard RT table tops.

As shown in FIG. 17 specially designed handles 38 are provided to quickly and easily attach to the side rails 22A and 22B of the patient support panel for facilitating the manual lifting and transporting of the patient support panel with the patient thereon. The handles 38 are best seen in FIG. 17A and basically comprise a cylindrical hand-grasp member 40 having a pair of yokes 42 at opposite ends of the member 40. A semi-circular bar 44 is connected to the free end of each of the yokes and forms the upper jaw of a clamp mechanism. The clamp mechanism also includes a lower jaw 46, which is pivotably connected to the hand-grasp member 40. A spring-biased plunger 48 has a free end (not shown) which is adapted to be disposed within any one of the indexing apertures 24 in either of the side rails 22A or 22B of the patient support panel 22. With the plunger 48 in place in any of the indexing apertures 24 the handle 38 is resistant to longitudinal displacement. Lifting upward on the hand-grasp member 40 has the effect of bringing the upper jaw downward toward the lower jaw, thereby tightly clamping the side rail 22A or 22B between those jaws. Thus, the handle 38 can be used to readily and safely manually lift the patient support panel 22 with a patient in any situation.

Figure 8:
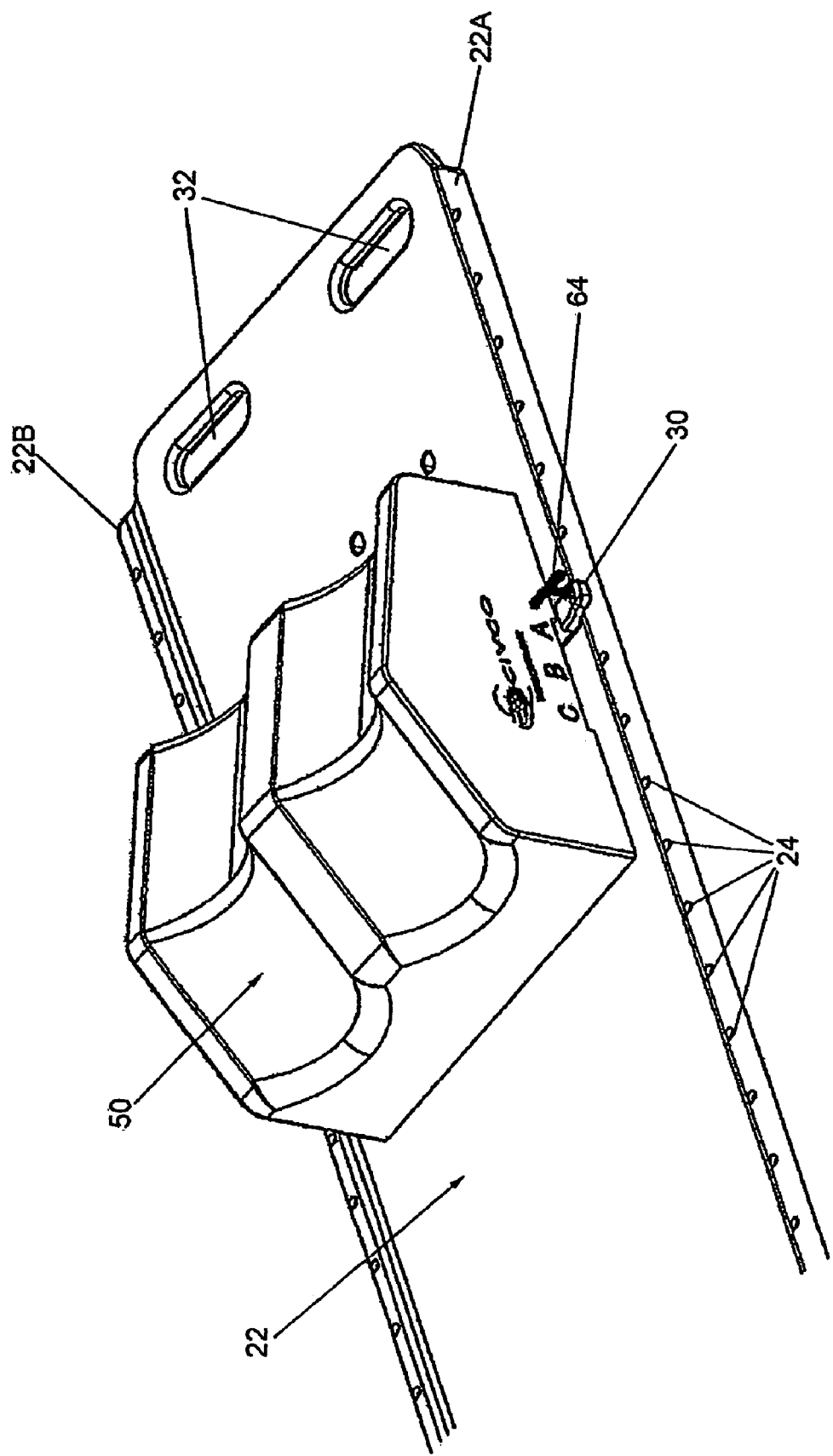
FIG. 8 is an isometric view of a patient support panel constructed in accordance with this invention on which a conventional leg positioning cushion is mounted utilizing a locking bar constructed in accordance with this invention.

Almost any variety of positioning and/or immobilizing (positioning/fixation) equipment currently on the market that utilizes the pin localizing method can be use on the patient support panel 22 or on the rail frame 200. Thus, many types of head frames or head supports or other positioning/fixation components may be affixed to the table top or rails as desired. For example, as best seen in FIGS. 1, 8 and 9 a conventional knee support cushion 50, such as that sold by CIVCO under the trademark KNEE-LOK, and a conventional foot support cushion 52, such as that sold by CIVCO under the trademark FOOT-LOK, may be releasably attached to the side rails 22A and 22B of the patient support panel 22 by respective two-pin locking bars 30. Each two-pin locking bar 30 is similar in construction to a conventional two-pin locking bar, like that sold by CIVCO under the trademark LOK-BAR, except that the ends of the bar include releasable fastening push pins for releasable engagement with the apertures in the patient support panel 22 or the apertures in the rails (to be described) of the rail frame 200. Thus, as best seen in FIG. 10, the locking bar 30 basically comprises an elongated flat bar 60 having a respective push-pin end piece 62 on each of its ends. Each end piece 62 includes a generally T-shaped push pin 64 extending therethrough. The push pins are of conventional construction sold by CIVCO under the trademark SAFE-T PINS. Each end piece includes a projecting free end portion 66 (FIG. 10) that is arranged to be disposed within any of the indexing apertures 24 in the rails 22A and 22B of the patient support panel 22 or in the corresponding apertures in the rails of the rail frame 200. Each free end 66 is arranged to expand (flare outward) when the T-shaped head of the pin is pressed/ twisted, whereupon it frictionally engages the aperture 24 in which it is located to hold the locking bar 30 in place at that indexing point. As is conventional the locking bar also includes a pair of registration pins 68 projecting upward from it for receipt within respective apertures or holes in the component to be mounted thereon. For example, as shown in FIG. 11 the knee cushion 50 includes a slot 70 with spaced holes 72 in its undersurface to receive the lock bar 60 and the registration pins 68. Stereotactic frames may also be attached to the lock bar 30. In fact many components that may be attached to conventional two or three pin locking bars can be attached to the lock bars 30 of this invention.

As will be appreciated from the discussion to follow many of the positioning/fixation devices/components constructed in accordance with this invention are arranged to be releasably mounted on the patient support panel 22 or on the rail frame 200 so that a portion extending above the prone patient will press down on a portion of the patient's body to restrict the movement of that portion of the patient's body or otherwise immobilize it. Examples of such devices are the heretofore identified devices/components 80 and 100, as well as the devices/components shown in FIGS. 7, 13-16, 20, 21. All of those devices/components are typically to be used in combination with a pad or cushion, like the pad 120, disposed on the patient support panel 22. The pads/cushions serve to provide a conformable support surface for the patient to lie upon, such as shown in FIG. 1, and can extend the full length of the patient support panel 22 or only a portion of it, e.g., the torso-length component 120. In any case, it is preferable that the cushions/pads be adapted to conform to the contours of the patient's body and to remain in that configuration for the duration of the SBRT. CIVCO sells vacuum actuated cushions/pads to accomplish that end under the trademark VAC-LOC. The VAC-LOC™ cushion/pad is a hollow flexible member or bladder that is filled with a multitude of polystyrene beads to create a rigid, comfortable cradle around the patient when vacuum is drawn through a quick release valve.

Figure 4:
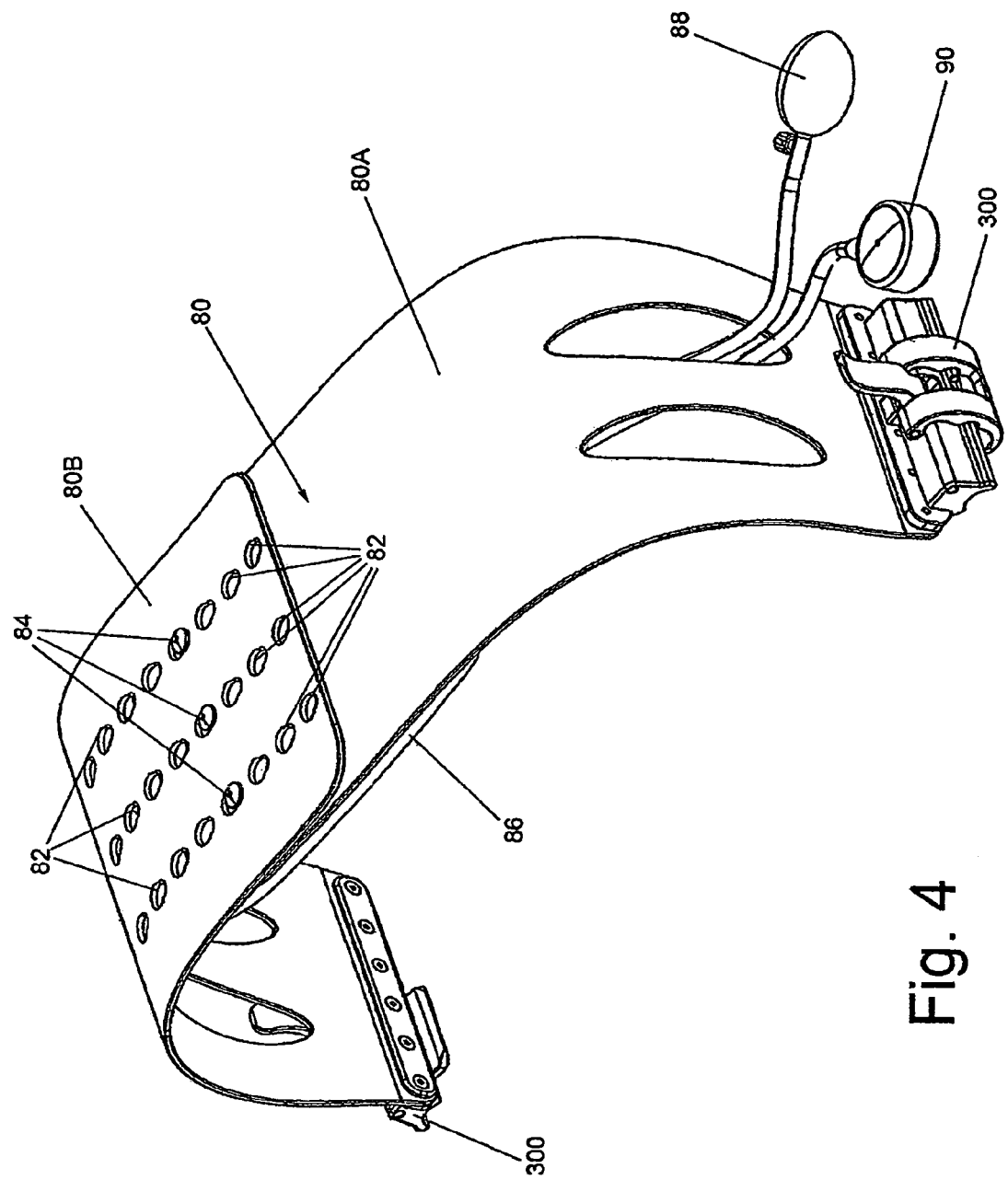
FIG. 4 is an enlarged isometric view of the exemplary, pneumatically operated positioning/fixation device for restricting respiratory excursion, like shown in FIG. 1, constructed in accordance with this invention.
Figure 5:
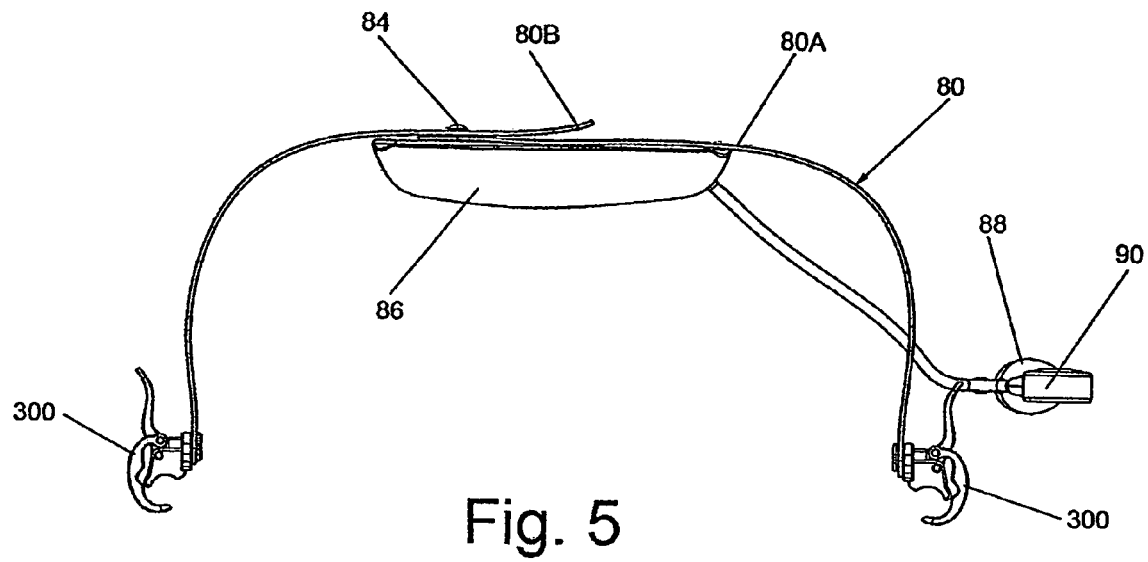
FIG. 5 is a reduced, front elevation view of the positioning/fixation device shown in FIG. 4.

Referring now to FIGS. 1, 4 and 5, the heretofore identified pneumatically operated respiratory restriction device 80 will now be described. This device is used to minimize diaphragmatic excursions which could interfere with radiation therapy directed to the chest or abdomen. By controlling the degree diaphragmatic excursion one can limit the movement of internal organs that move with the diaphragm. The device 80 is arranged to be located at any longitudinal position along the patient support panel 22 by virtue of its clamping mechanisms (to be described later). Thus, one can form fit the device 80 (or any of the other positioning/fixation components) precisely to the desired region of a patient's anatomy to achieve comfortable and very effective immobilization, i.e., create an effective patient immobilization sandwich comprising a top layer formed by the device 80 in concert with the vacuum cushion 120 disposed underneath the patient.

Figure 22:
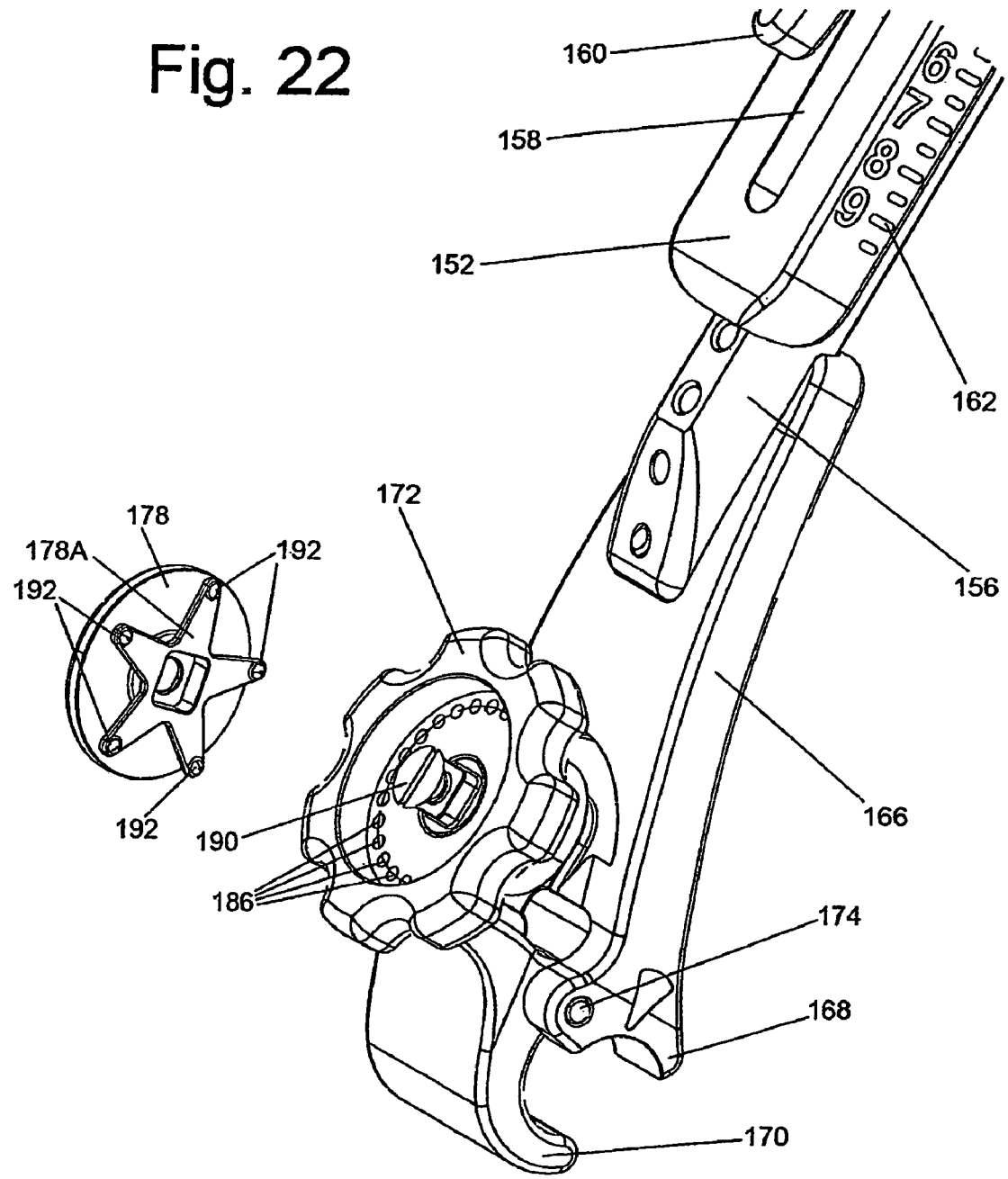
FIG. 22 is an enlarged exploded isometric view of the clamp mechanism portion of the universal bridge component of FIG. 7 showing the details of that clamping mechanism.
Figure 23:
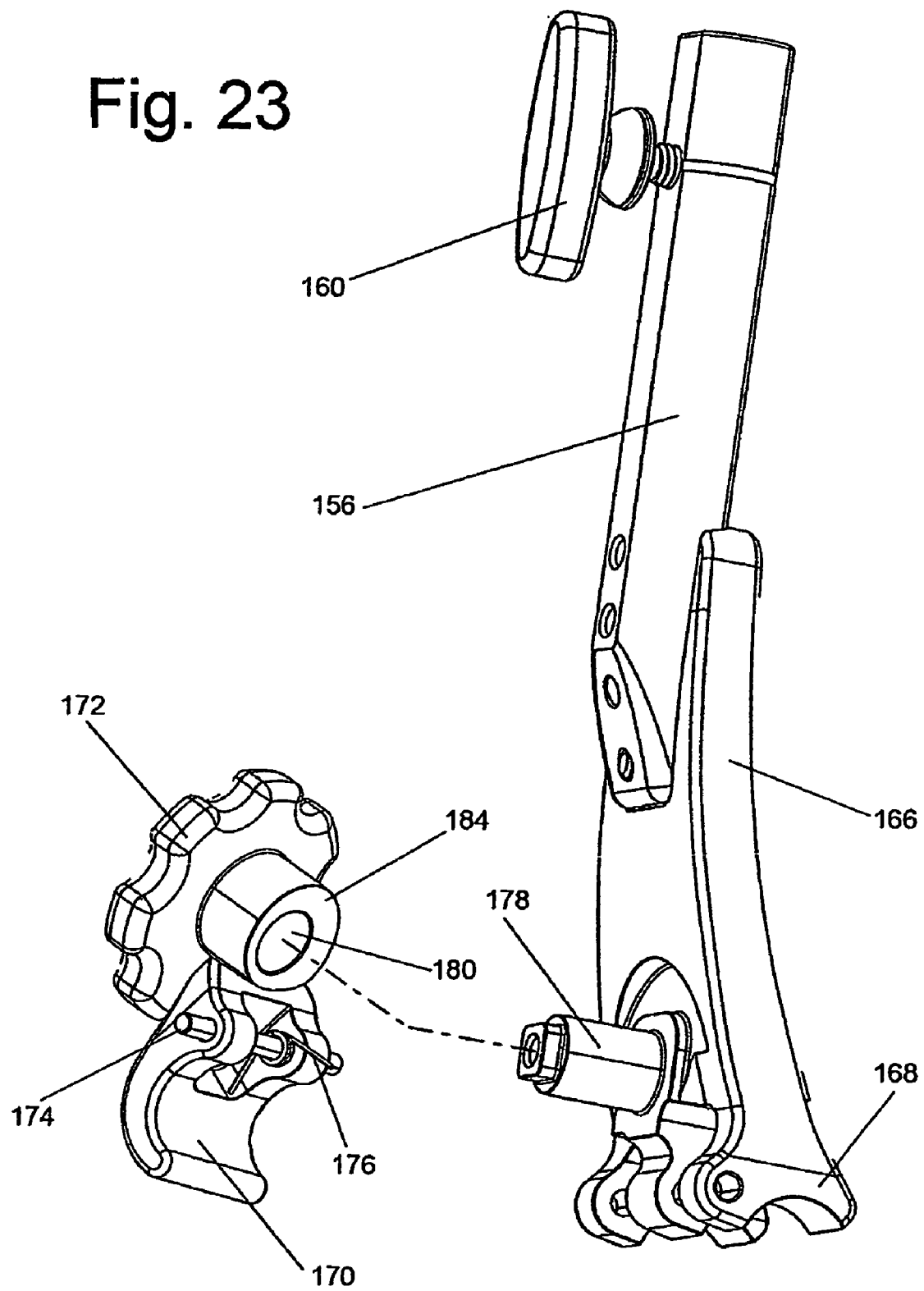
FIG. 23 is an enlarged exploded isometric view of the portion of the bridge component shown in FIG. 22, but taken from a different direction.

The device 80 basically comprises a belt-like member formed of a pair of somewhat flexible sheets 80A and 80B, each of which includes a clamp mechanism at its lower end. The belt like member 80 is arranged to be releasably mounted by those clamp mechanisms to the rails of the patient support panel 22 or to the rails of the rail frame 200 anywhere along the axis of the patient using the index indicia on the rails. Each clamp mechanism shown in those figures is represented as being the heretofore mentioned over-center levered latch mechanism similar to that used on the patient handles shown in FIGS. 2, 2A and 2B. While such a clamp mechanism can be used for those applications, it is preferable to use the cam tensioner clamping mechanism like that shown in FIGS. 22 and 23. In fact, for most applications that require a clamp mechanism to provide releasable securement of the positioning/fixation component, the cam tensioner clamp mechanism of FIGS. 22 and 23 is preferred.

The flexible sheets 80A and 80B of the belt member 80 are arranged so that their free ends can be overlapped by a desired amount respect to each other to accommodate patients of differing anatomic sizes, shapes and proportions. To that end, the flexible sheets of the belt-like member 80 include index marks for establishing an initial tightening (overlap) position. In order to hold the overlapped sheets in place with respect to each other plural rows of apertures or key holes 82 are provided in the free end portion of the sheet 80B and a row of upstanding buttons 84 is provided in the free end portion of the sheet 80A. The buttons 84 are arranged for insertion into the key holes 82. In particular, with the sheets overlapped to the degree appropriate for a particular patient, a row of the key holes 82 of the sheet 80B will be aligned with the row of buttons 84 of the sheet 80A, whereupon those buttons can then be inserted into the aligned key holes to releasably secure the overlapping free ends of the sheets 80A and 80B together.

An inflatable bladder 86 (FIG. 5) is mounted on the underside of sheet 80A for engagement with the epigastric area of the patient. The bladder 86 is arranged to be inflated by a hand pump (bulb) 88 and the pressure within the bladder measured by a pressure gauge 90. Thus, one can pump the bladder up until it is at a desired pressure so that the appropriate degree of restriction of the patient's diaphragmatic excursions can be established.

Figure 20:
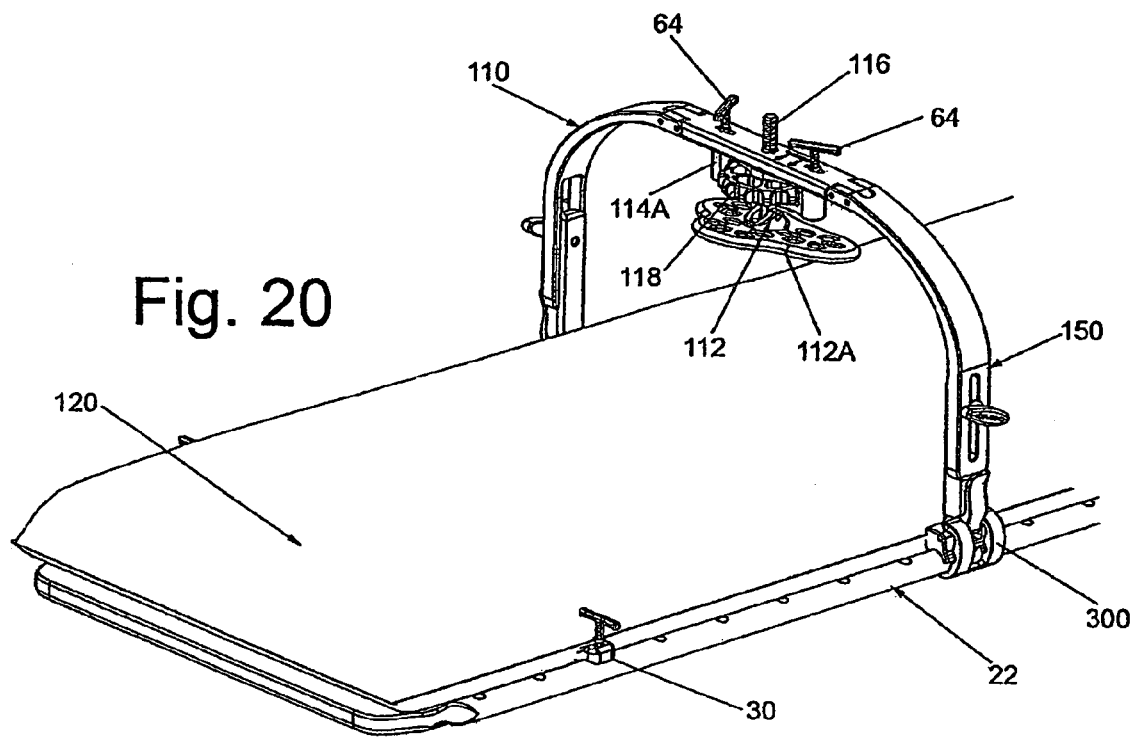
FIG. 20 is an isometric view of a portion of an exemplary embodiment of a mechanically operated positioning/fixation device for restricting respiratory excursion constructed in accordance with this invention.
Figure 21:
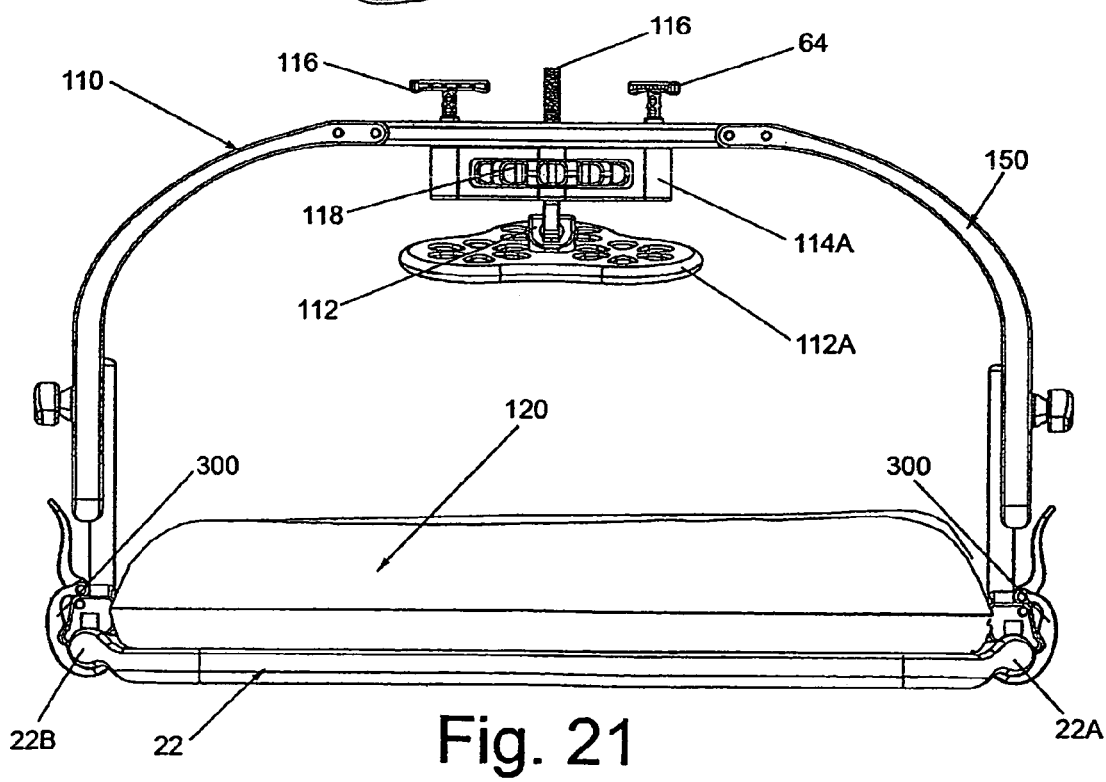
FIG. 21 is an enlarged front elevation view of the system shown in FIG. 20.

If mechanical respiratory restriction is desirable in lieu of the pneumatic restriction provided by the device 80, a bridge mounted mechanical positioning/fixation device 110 can be used with the patient support panel 22. The device 110 is shown in FIGS. 20 and 21 and basically comprises an adjustable pressure plate assembly 112 mounted on a universal bridge component 150. The pressure plate assembly basically comprises a plate 112A mounted via a threaded screw 116 to a central portion of the universal bridge component 150 for external compression in the epigastric area of the patient.

Figure 7:
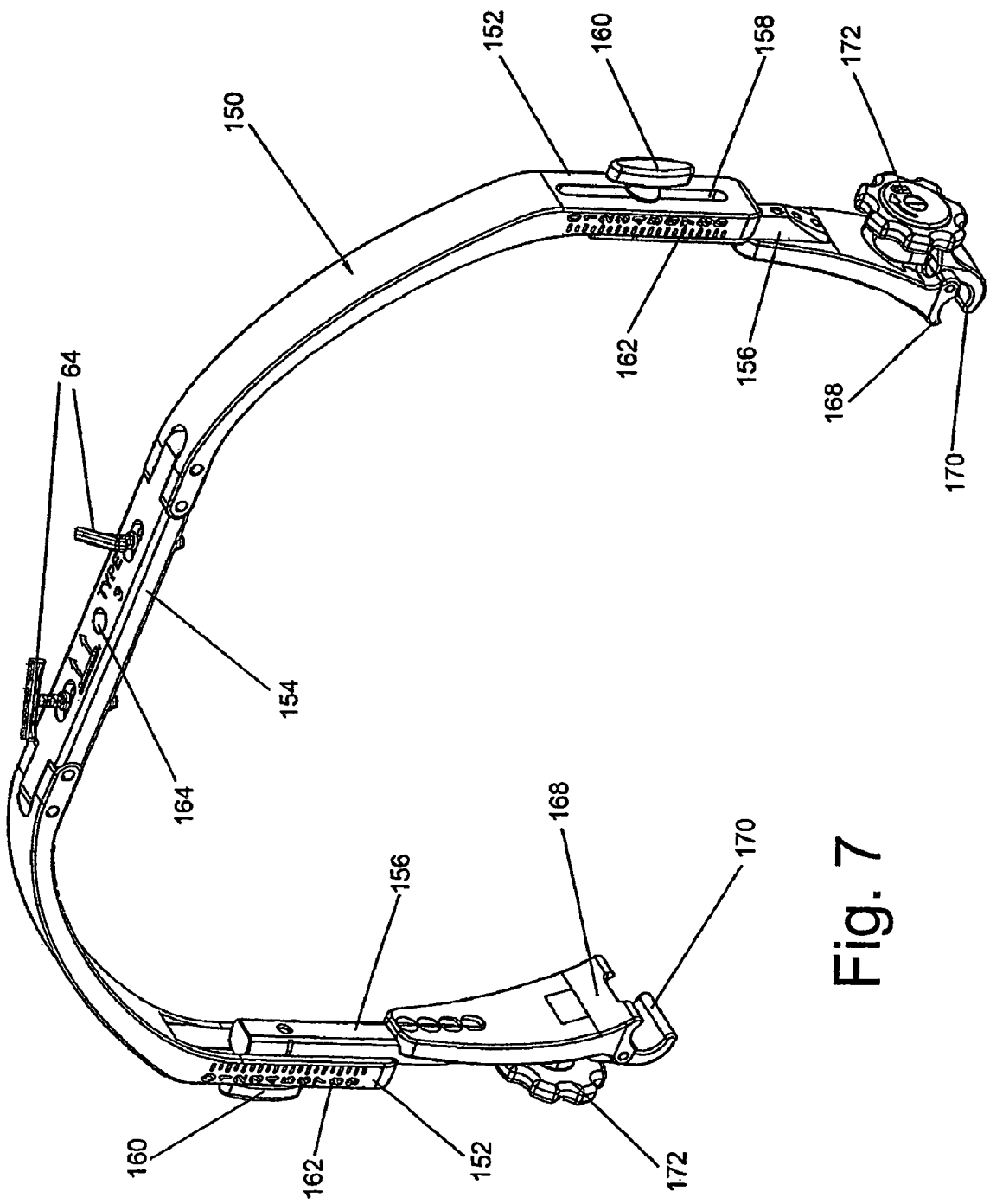
FIG. 7 is an enlarged isometric view of the universal bridge component making up the system of this invention and arranged for releasable securement to a patient support panel constructed in accordance with this invention.

Before describing the details of the mechanical respiratory restriction device 110 further, a description of the universal bridge 150 is in order. It is called a "universal" bridge inasmuch as it can be used to mount a multitude of positioning/fixation devices on it. The universal bridge 150 is best seen in FIG. 7 and basically comprises a pair of vertically extending side legs 152 and an intermediate or central section 154. The lower end of each of the side legs 152 is arranged to mount a respective clamp mechanism thereon. The clamp mechanisms will be described later and are preferably the cam tensioner type shown in FIGS. 22 and 23. Suffice it for now to state that each includes an elongated post 156 which is adapted to be slidably secured to the lower end portion of a respective side leg 152 to adjust the height of the bridge with respect to the patient support panel 22 on which it will be mounted. In particular, the lower end portion of each side leg 152 includes a slot 158 through which a threaded thumb screw 160 extends. When the threaded thumb screw is loosened the post 156 of the clamp mechanism can be slid either up or down with respect to the side leg 152, thereby establishing the height of the bridge. To facilitate the setting of the height of the bridge indicia 162 is provided on each side leg.

The central section 154 of the bridge includes an opening 164 through which the threaded screw 116 of the restriction assembly 112 extends. The opening 164 can also be used to accommodate any threaded member or other component mounting member to adjustably support any component or assembly on the bridge. In addition, and in the interest of modularity, the central portion 154 of the bridge includes a pair of push pins 64, like those used with the locking bar 30. The push pins 64 serve to fixedly mount any of a number of components or assemblies onto the bridge. For example, the restriction assembly 112 includes a housing 114A which is mounted on the underside of the central section 154 of the bridge via a pair of push pins 64. The housing 114A includes a slot in which a thumb wheel 118 is disposed. The thumb wheel 118 includes a threaded hole through which the threaded screw 116 extends. The upper end of the threaded screw extends through a hole (not shown) in the housing 114A and through the hole 164 in the central section 154 of the bridge. The lower end of the threaded screw 116 is in the form of a pivotal joint mounting the pressure plate 112A thereon.

In use, the height of the bridge will initially be set by adjusting the height of its legs as described earlier. Once that has been accomplished the thumb wheel 118 can be rotated to establish the precise amount of pressure on the patient's diaphragm to comfortably immobilize the patient's abdomen. In particular, to mechanically adjust the plate 112A with respect to the bridge all that is required is to rotate the thumb wheel in the desired rotational direction to bring the plate either closer or further from the central section of the bridge.

As mentioned earlier, the preferred clamping mechanisms for the various components of the system 20 is the cam tensioner which is best seen in FIGS. 22 and 23, but also shown in FIGS. 7, 16A, 16B, 26 and 27. Basically it comprises the heretofore identified post 156, a somewhat arcuate elongated body 166 terminating in its lower end in an upper jaw 168, a lower jaw 170, a rotary knob 172, a pivot pin 174, a biasing spring 176 and a detent assembly (to be described later). As best seen in FIG. 23 the outside surface of the body 166 includes a cylindrical shaft or post 178 projecting outward. The shaft 178 is arranged to be received within a central opening 180 in a cam portion 184 projecting inward from the inner surface of the knob 172. The lower jaw 170 is pivotably connected to the upper jaw 168 via the pivot pin 174 and is normally biased in the open position by the spring 176. The cam portion 184 includes a surface engaging the upper portion of the lower jaw above its pivot axis. Thus, when the knob is rotated in the clockwise direction the cam surface presses downward on the top surface of the lower jaw to cause that jaw to pivot towards the upper jaw against the bias of the spring 176, thereby closing the clamp mechanism. In order to ensure that the jaws remain in the closed position the heretofore identified detent assembly is provided. That assembly basically comprises a circular cap member 178 including a star-like detent washer 178A and a plurality of semicircular pits or dimples 186 arranged in a circular array within a central recess in the knob 172. The circular cap 178 with its star-like detent washer 178A projecting inward from its inner surface is arranged to be received within the central recess of the knob 172 and fixedly secured to the shaft 180 by a threaded screw 190. The free end of the shaft 178 is of square shape and is arranged to fit within a correspondingly shaped opening in the detent washer 178A so that when the cap with its detent washer is secured to the shaft by the screw 190 the cap cannot rotate with respect to the shaft. The free end of each of the prongs of the star-like washer 178A includes a semispherical projection 192 of corresponding size and shape to each of the dimples or pits 186. Thus, when the knob 172 is rotated to a position to cause the jaws of the clamp mechanism to close the semispherical projections will be seated in respective ones of the dimples in the knob to deter the jaws from tending to spring open. When opening of the jaws is desired, all that is necessary is to rotate the knob in the opposite direction with sufficient force to overcome the holding force of the detent mechanism, whereupon the jaws will open and the bridge (or other member of which the clamp mechanism is a part) can be slid longitudinally on the rails of the patient support panel to a desired position or the bridge can be removed.

Figure 6:
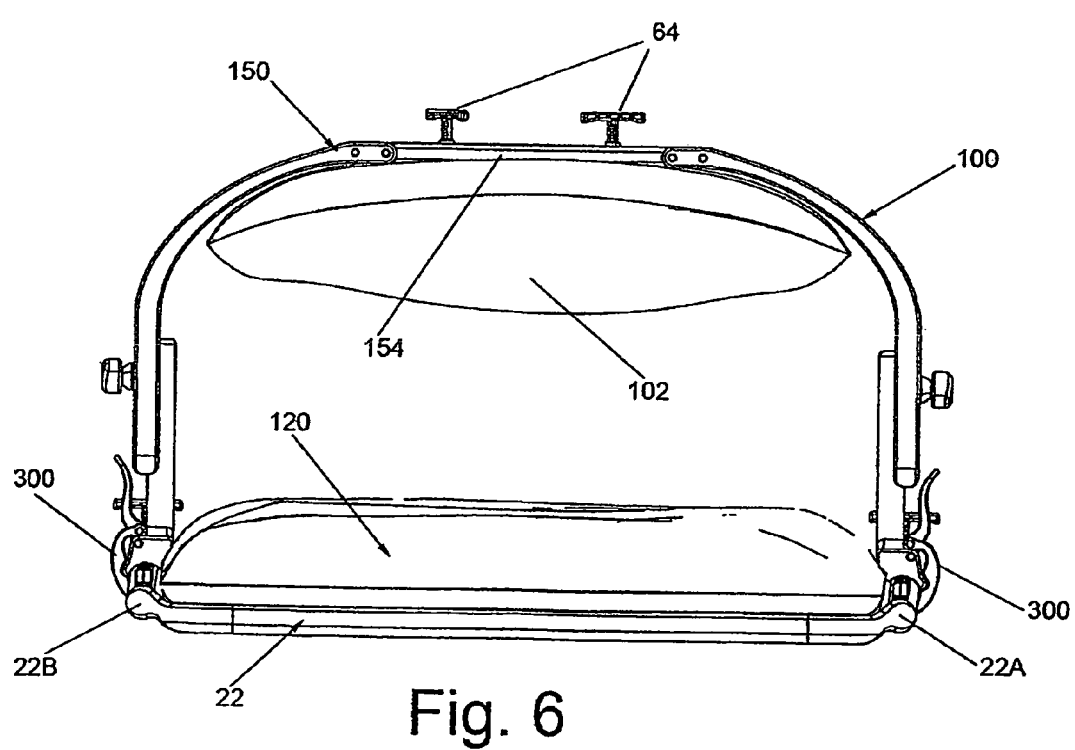
FIG. 6 is a front elevation view of a positioning/fixation device making use of an exemplary embodiment of a universal bridge of this invention shown mounted on the patient support panel having a vacuum operated conformable cushion mounted thereon on which the patient is disposed.

Referring now to FIG. 6, the details of the leg positioning/fixation device 100 as an example of one use of the top cushion arrangement will now be described. That device basically comprises the heretofore identified universal bridge 150 on which a conformable vacuum operated cushion 102 is mounted. The cushion 102 is a rectangular member of similar construction to the cushion/pad 120 except that it is considerably smaller in size. The cushion 102 is mounted on the central section 154 of the universal bridge 150 via a pair of push pins 64. The leg positioning/fixation bridge 100 is particularly effective for immobilizing a patient's legs when it is used with a leg positioning cushion 50 and a foot positioning cushion 52 like shown in FIG. 1. However, it can be used alone or with other types of cushions, if desired. Moreover, it is not limited to holding down the legs. Thus, it can be used to fix the hips or shoulders of a patient.

Figure 13:
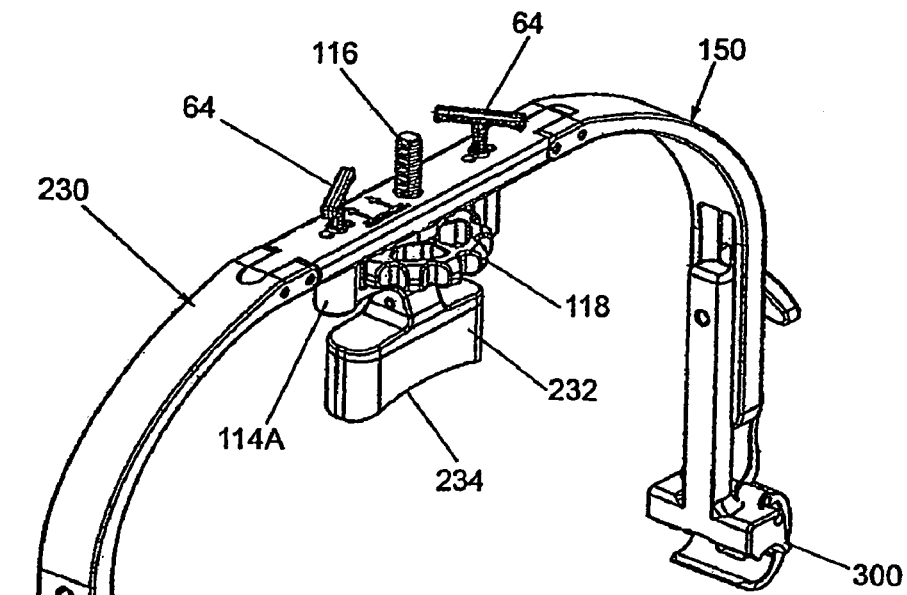
FIG. 13 is an isometric view of one of the bridge members, i.e., the head restraint member, shown in FIG. 12.
Figure 14:
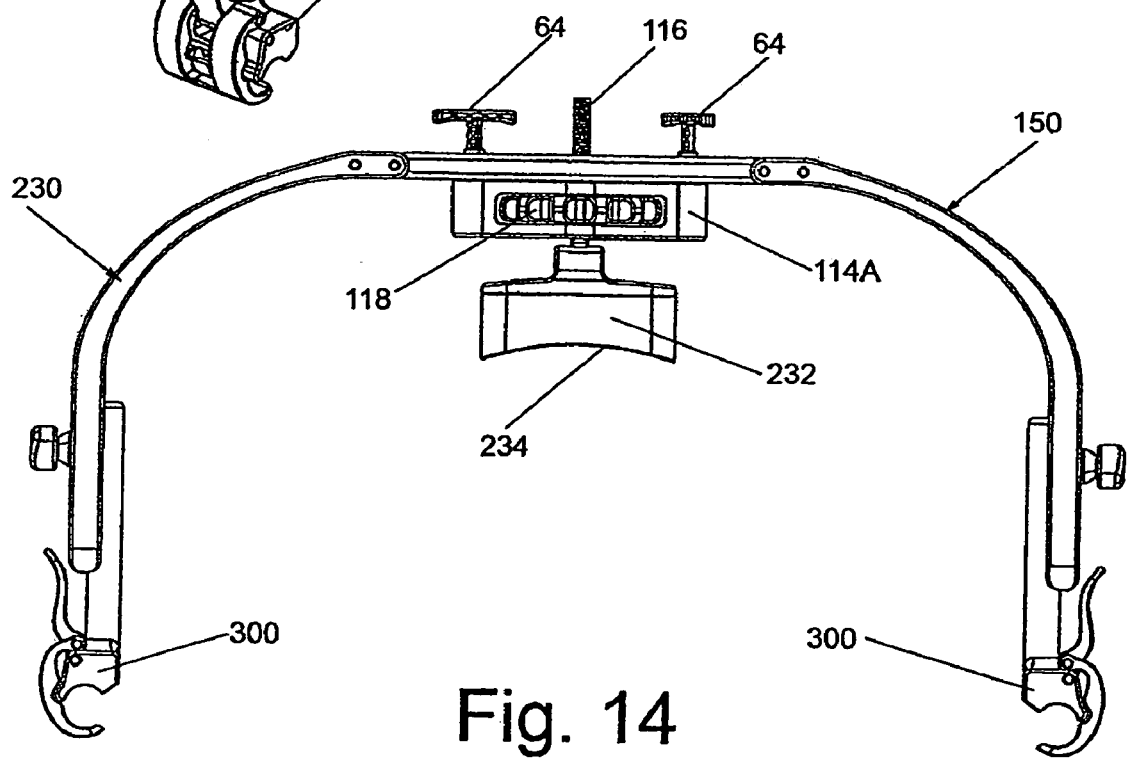
FIG. 14 is a front elevation view of the bridge member shown in FIG. 13.

Referring now to FIGS. 12-14, a skull positioning/fixation device 230 will now be described. That device basically comprises the heretofore identified universal bridge 150 on which an adjustable forehead engaging cushion assembly 232 is mounted. The adjustable forehead engaging cushion assembly 232 is somewhat similar in construction to the adjustable pressure plate assembly 112 of the mechanical respiratory restricting device 110, except for the substitution of a cushion 234 for the pressure plate 112A. In particular, the cushion 234 basically comprises closed-cell foam disposed about a rigid core. The lower end of the threaded screw 116 is fixedly connected to the core. The cushion is arranged to press down on the forehead to help immobilize the skull of the patient. To that end, the undersurface of the cushion is of a concave shape to readily accommodate the forehead of the patient. By twisting the thumb wheel 118 in either the counterclockwise or clockwise direction the cushion 234 can be brought closer or further away from the forehead of the patient. In use, the height of the device 230 will initially be set by adjusting the height of its legs as described earlier. Once that has been accomplished the thumb wheel 118 will be rotated to bring the cushion 234 into engagement with the patient's forehead, with the precise amount of pressure to comfortably immobilize the skull.

Figure 15:
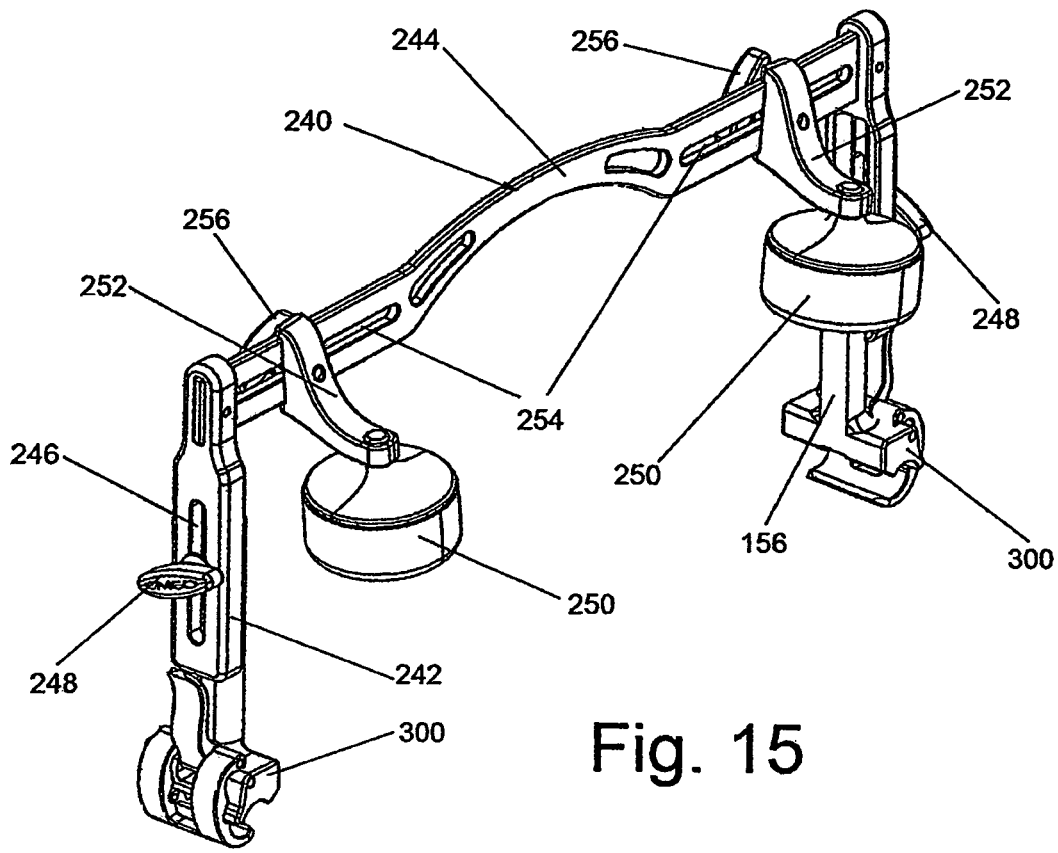
FIG. 15 is an isometric view of the other of the bridge members, i.e., a shoulder positioning/fixation device, shown in FIG. 12.
Figure 16:
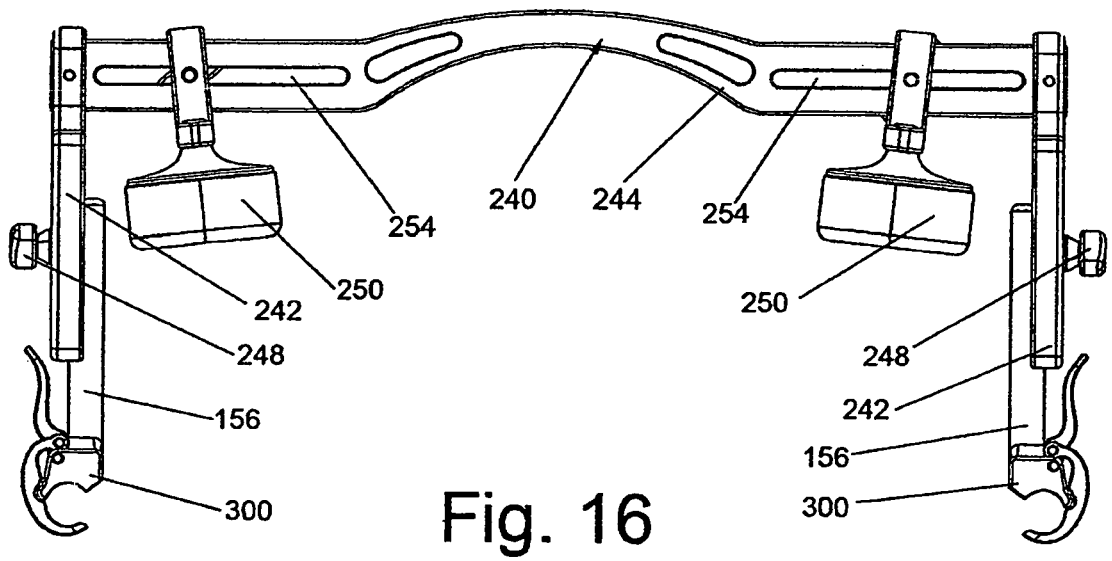
FIG. 16 is a front elevation view of the bridge member shown in FIG. 15.

Referring now to FIGS. 12, 15 and 16, a shoulder positioning/fixation device 240 will now be described. The device 240 is a dedicated unit that basically comprises a pair of vertically extending side legs 242 and an intermediate or central section 244. The lower end of each of the side legs 242 is arranged to mount a respective clamp mechanism thereon. The clamp mechanisms are preferably the cam tensioner type like disclosed heretofore with respect to FIGS. 22 and 23, but may be of the over center latch type 300 as will be described later. Suffice it for now to state that in either case the clamping mechanism includes an elongated post 156 which is adapted to be slidably secured to the lower end portion of a respective side leg 242 of the device 240 to adjust the height of the device with respect to the patient support panel 22 on which it is mounted. In particular, the lower end portion of each side leg 242 includes a slot 246 through which a threaded screw 248 extends. When the threaded screw is loosened the post 156 of the clamp mechanism can be slid either up or down with respect to the side leg 242, thereby establishing the height of the device. To facilitate the setting of the height of the device indicia (not shown) may be provided on its side legs.

A pair of shoulder-engaging cushions 250 is mounted on respective end portions of the central section 244 by respective brackets 252. The spacing between the shoulder-engaging cushions is adjustable to accommodate patients of differing anatomic sizes, shapes and proportions. To that end, each bracket is mounted on a respective slot 254 in the central section by means of an adjustable thumbscrew 256. When the thumbscrew is loosened the bracket with the cushion 250 mounted thereon can be slid to any transverse position within the associated slot 254, whereupon the thumbscrew can be tightened to fix the cushion in that transverse position.

As mentioned earlier, a preferred clamp mechanism for the various components of this invention is the cam tensioner shown in FIGS. 22 and 23. A less preferred, but still viable, clamping mechanism is the over-the-center latch shown as part of the patient positioning handles 36 in FIGS. 2A and 2B and designated by the reference number 300. For illustrative purposes the clamping mechanism 300 is shown as making up the clamping mechanisms of the devices 80, 100, 230 and 240, it being understood that the screw tensioner clamping mechanism shown in FIGS. 22 and 23 is the preferred mechanism for those devices.

Referring now to FIGS. 2A and 2B the details of the over-center latch clamping mechanism 300 will now be described. That clamping mechanism basically comprises an upper jaw member 302, a lower jaw member 304, a latch handle 306, a first pivot pin 308 and a second pivot pin 310. The latch handle is a lever-like member having an upper opening 312 and a lower opening 314. The lower jaw includes a bifurcated upper portion having axial aligned openings 316. The axially aligned openings 316 are arranged to be aligned with the upper opening 312 in the latch handle 306, with the pivot pin 310 extending through those aligned openings to pivotably connect the lower jaw to the latch handle. The upper jaw is also bifurcated and includes axial aligned openings 318. The axially aligned openings 318 are arranged to be aligned with the lower opening 314 in the latch handle 306, with the pivot pin 308 extending through those aligned openings to pivotably connect the latch handle to the upper jaw. As will be appreciated by those skilled in the art the foregoing arrangement creates an over-center latch clamp, which when the latch handle is pivoted upward causes the jaws to move towards each other to a closed position like shown in FIG. 2A.

The upper jaw has a concave surface of a shape complementary to the profile of the rails 22A and 22B. The lower jaw also has a concave surface of a shape complementary to the profile of the rails 22A and 22B. Thus, when the jaws are closed they will tightly engage the periphery of the rail portion between them to releasably secure the clamp to that rail. In order to release the clamping mechanism 300 all that is required is to pivot the latch handle downward 306, whereupon the jaws open to enable the device on which the clamping mechanism is mounted to be slid along the rail of the patient support panel to a different longitudinal position or to enable that device to be removed.

Figures 16A, 16B:
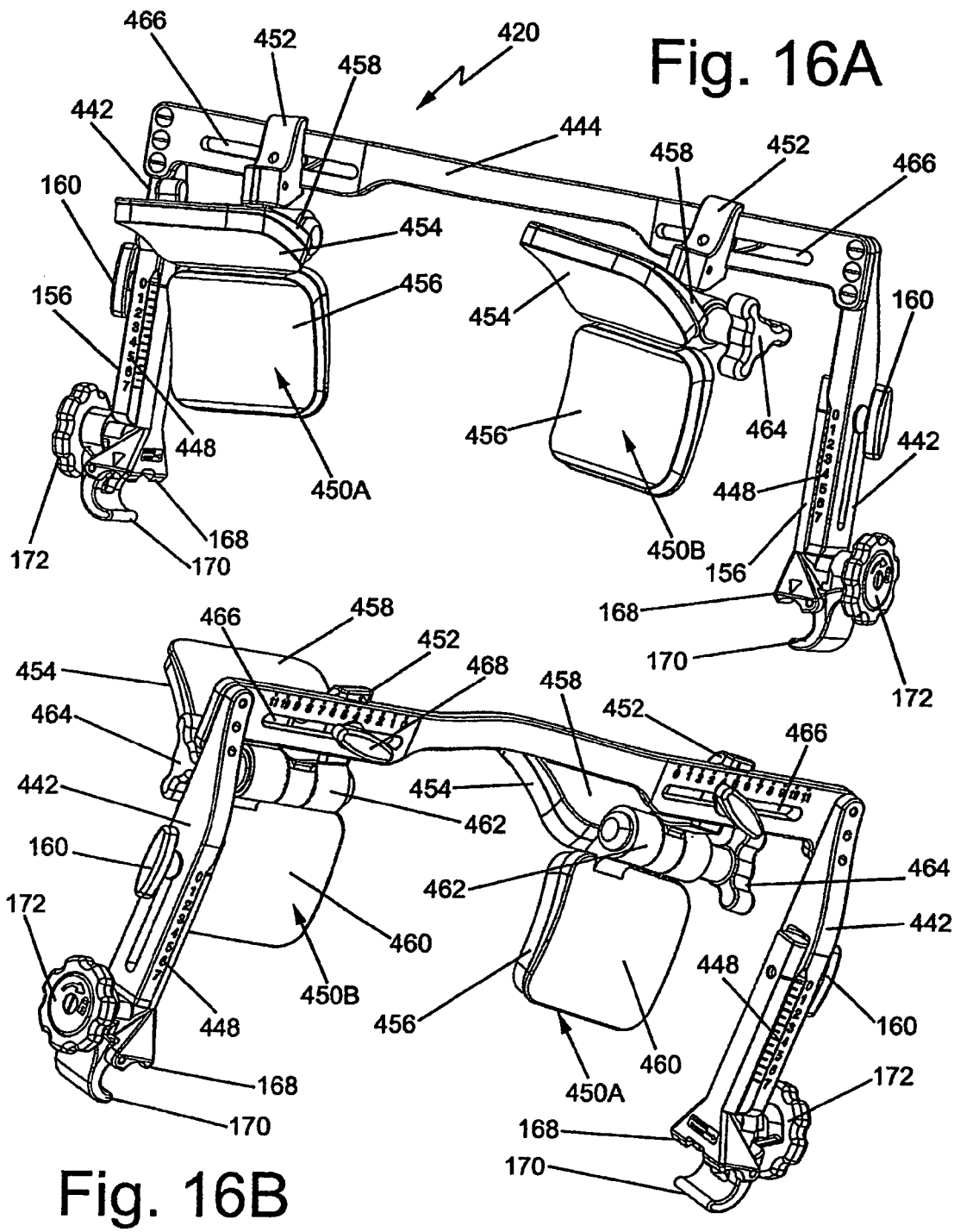
FIG. 16A is a front isometric view of an alternative shoulder positioning/fixation device constructed in accordance with this invention.
FIG. 16B is a rear isometric view of the shoulder positioning/fixation device shown in FIG. 16A.

Referring now to FIGS. 16 and 16B, an alternative shoulder positioning/fixation device 440 will now be described. The device 440 is a dedicated unit that basically comprises a pair of vertically extending side legs 442 and an intermediate or central section 444. The lower end of each of the side legs 242 is arranged to mount a respective clamp mechanism thereon. The clamp mechanisms are preferably the cam tensioner type like disclosed heretofore with respect to FIGS. 22 and 23, but may be of the over center latch type 300 as described earlier. Suffice it for now to state that in either case the clamping mechanism includes an elongated post 156 which is adapted to be slidably secured to the lower end portion of a respective side leg 442 of the device 440 to adjust the height of the device with respect to the patient support panel 22 on which it is mounted. In particular, the lower end portion of each side leg 442 includes a slot 246 through which a threaded thumb screw 160 extends. When the threaded thumb screw is loosened the post 156 of the clamp mechanism can be slid either up or down with respect to the side leg 242, thereby establishing the height of the device 440. To facilitate the setting of the height of the device indicia 448 is provided on each of its side legs 242.

A pair of shoulder-engaging cushion assemblies 450A and 450B is mounted on the central section 444 of the bridge device 440 by respective brackets 452. Each assembly includes a pair of cushions 454 and 456. The cushions 454 and 456 are secured to respective slightly curved plates 458 and 460. The plates 458 and 460 are pivotably connected to each other at a hinge joint 462 to enable one to adjust the angular relationship between the plates 458 and 460 to accommodate the shoulders of patients of various sizes, shapes and proportions. To that end, the hinge joint 462 includes a tightenable handle 464 which when tightened fixes the angle between the plates 458 and 460. Untightening the handle 464 enables the angle between the plates (and the cushions mounted) thereon to be set at another angle for a different patient. The spacing between the cushion assemblies 450A and 450B is also adjustable to accommodate patients of differing anatomic sizes, shapes and proportions. To that end, each bracket is mounted on a respective slot 466 in the central section 444 by means of a threaded thumbscrew 468. When its thumbscrew 468 is loosened the bracket 452 with the cushion assembly mounted thereon can be slid to any transverse position within the associated slot 466, whereupon the thumbscrew 468 can be tightened to fix the cushion assembly in that transverse position.

In FIGS. 17-19 there is shown a fiducial box or frame device 280 arranged to be mounted on the patient support panel 22 by means of push pins 64. The device 280 includes a frame 282 arranged for surrounding a portion of the patient on which geometrically oriented radio-opaque (visible on x-ray) or optical markers 284 are disposed. The frame includes four legs, each of which terminates at its lower end in a connector member 286 constructed similar to the end members 62 of the locking bar 30. A respective push pin 64 extends through each connector to expand a projecting portion (not shown) of that connector within an associate indexing aperture 24 in the side rails of the patient support panel. The legs on each side of the frame 282 are spaced by an integer multiple of the 7 cm spacing between the indexing apertures 24 of the rails 22A and 22B so that the fiducial frame device 280 can be located at desired discrete longitudinal positions along the patient support panel as defined by the indexing apertures 24. When so mounted the device 280 will serve to verify the precise location of the SBRT patient support panel 22 and the patient/target tumor relative to the treatment beam isocenter.

As mentioned earlier, the rail sections 22A and 22B that are an integral part of the patient support panel, and which serve as the attachment area for many of the SBRT components can also be made in a free-form or stand-alone configuration that can be adapted to fit directly to a non-SBRT specific treatment couch (i.e., a generic treatment couch made by CIVCO, Varian, Elekta, or other vendors). Two exemplary embodiments of that stand-alone configuration 200 are shown in FIGS. 24 and 25. Each embodiment is in the form of a frame 200 having a pair of side rails 222A and 222B. The rails 222A and 222B are constructed like the rails 22A and 22B and thus include the indexing apertures 24 and indexing indicia therealong. When the frame 200 is mounted on the conventional couchtop all of the other modular components of the system 20 of this invention can be mounted thereon. Thus, all the components designed specifically for the SBRT patient support panel 22 can be used on a standard treatment couchtop without using the patient support panel 22. This is advantageous in that the rail frame embodiment 200 eliminates the extra layer of the SBRT patient support panel, while still allowing all the positioning and immobilizing functionality of the modular components except patient transfer (and set-up outside the treatment room). The rail frame embodiment 200 shown in FIG. 24 is a half section, e.g., it is approximately 43 inches long, that can be used by itself for some applications, where full coverage of the treatment couchtop is not necessary or desirable. Alternatively, it can be coupled to a like half section 200, as shown in FIG. 25, to cover the entire treatment couchtop. This allows the user great flexibility to use the system to suit the user's specific needs for treating any anatomic site.

The rail frame 200 basically comprises the heretofore identified rails 222A and 222B and a pair of transversely extending wide cross bars 202 and 204. Each of the cross bars is an elongated member which is fixedly secured at its respective ends via a respective connector 206 to a respective one of the side rails 222A and 222B to form an integral unit. As mentioned above each of the side rails 222A and 222B is of similar construction to the side rails 22A and 22B so that the side rails 222A and 222B can mount the components of the system 20 thereon in the same manner as the side rails 22A and 22B mount those components on the patient support panel 22. Thus, in the interest of brevity the details of the construction and operation of the side rails 222A and 222B for mounting the component thereon will not be reiterated.

The rail frame 200 is arranged to be mounted on the conventional treatment couchtop via a universal two pin registration locking bar system provided with the couchtop. To that end, each of the cross bars 202 and 204 includes a pair of apertures 208 to accommodate the two registration pins of the couchtop lock bar. In particular, the couchtop lock bar (not shown) is releasably secured to the couchtop (not shown) at the desired position so that its two registration pins extend upward for receipt in the apertures 208 of the rail frame cross bar 202 or 204. In the embodiment shown in FIG. 24, an exemplary two pin registration lock bar 30 is shown mounted on the rail frame at an exemplary position via a respective pair of apertures in the rails 222A and 222B to serve to mount any component or device having comparable registration apertures thereon. The lock bar 30 can be mounted at any of the index position established by the pairs of apertures along the length of the rail frame 222A and 222B. In the embodiment shown in FIG. 25, two exemplary two pin registration lock bars 30 are shown mounted on the rail frame at exemplary positions via a respective pair of apertures in the rails 222A and 222B.

The cross bars 202 and 204 of the rail frame 200 are located to maintain consistent 14 mm spacing of the two pin indexing to existing couchtops. The rail frame's components can be formed of any suitable material, such as carbon fiber, fiberglass or epoxy.

Figure 26:
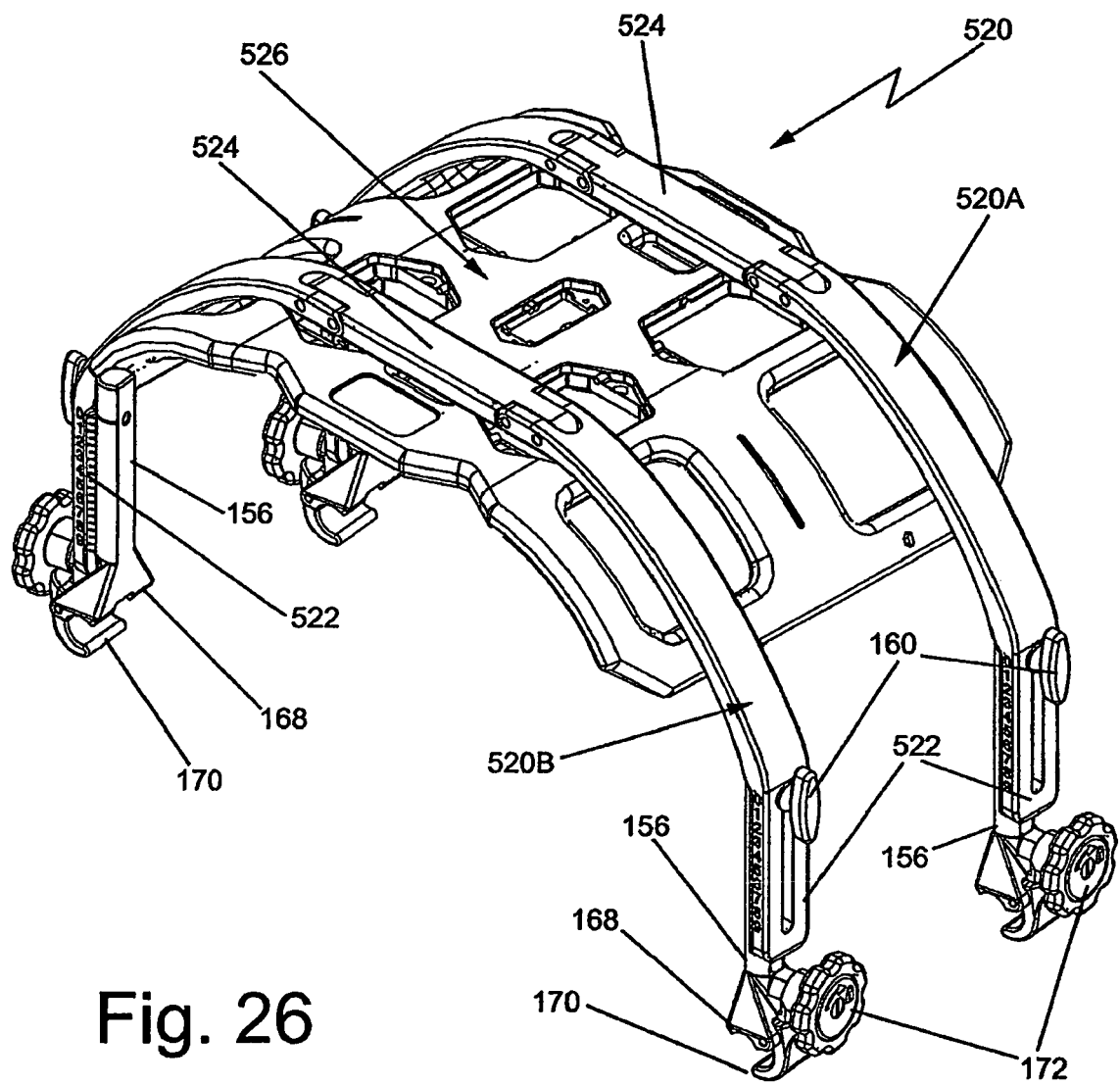
FIG. 26 is an isometric view of another bridge component, i.e., a MRI coil positioning device constructed in accordance with this invention.

In FIG. 26 there is shown another positioning device 520 constructed in accordance with an aspect of this invention. The positioning device 520 is arranged to be used in a system for positioning a patient for an MRI imaging procedure of the head or neck so that an MRI surface coil assembly can be located at a precise desired position with respect to the head or neck of the patient. That system thus includes a patient support panel on which the patient is disposed for the MRI imaging procedure. The patient support panel can be constructed similarly to the patient support panel 22 described above or can be any suitable patient couchtop/overlay provided by various suppliers. The exemplary embodiment of the positioning device 520 shown in FIG. 26 is particularly suited for use with the patient support panel 22. The device 520 is in the form of a pair of bridge member 520A and 520B, each of which comprises a pair of upstanding side legs 522 and a central section 524 bridging the legs. The lower end of each of the side legs 522 is arranged to mount a respective clamp mechanism thereon. The clamp mechanisms are preferably the cam tensioner type like disclosed heretofore with respect to FIGS. 22 and 23, but may be of the over center latch type 300 if desired. Each clamp mechanism includes an elongated post 156 slidably secured to the lower end portion of a respective side leg 522 of the device 520 to adjust the height of the central (bridging) section 524 of the device with respect to the patient support panel 22 on which it is mounted. Moreover, as described earlier, each clamp mechanism includes the a pair of jaws 168 and 170 which are arranged to grasp a respective portion of the side rails of the patient support panel 22 to enable the positioning device 520 to be releasably located at any longitudinal position along the patient support panel.

Any commercially available MRI surface coil assembly or device can be used with the bridge members 520A and 520B. Such devices are typically in the form of a frame or housing including one or more MRI coils (not shown) located therein. In the exemplary embodiment shown in FIG. 26 the MRI coil device is designated by the reference number 526 and is the type sold by Siemens, but could be those sold by Philips, Picker, GE Healthcare or other vendors. The device 526 is arranged to be releasably mounted by the positioning member 520A and 520B. In particular, one portion of the coil device 526 is mounted on the central or bridging section 524 of the member 520A and another portion of that device is mounted on the central section 524 of the member 520B. The coil device 526 is a generally flat, thin member that is somewhat conformable, i.e., it can be bent slightly to conform somewhat to the shape of the patient's head or neck at which it is to be held. The releasable securement of the frame 526 to the bridging members 520A and 520B is accomplished through the use of respective cooperating pairs of VELCRO® hook and loop fasteners (not shown) disposed at the interface of the coil device 526 and the underside of the central sections 524 of members 520A and 520B. Other type of releasable fastening devices can be used in place of the VELCRO® hook and loop fasteners. Irrespective of the type of releasable fastening means used, the use of releasable fastening means enables different types or sizes of MRI coil devices to be used with the bridge members 520A and 520B.

As will be appreciated by those skilled in the art, since the bridge members 520A and 520B can be positioned at any longitudinal position along the patient support panel 22 on which the patient is disposed, and since the height of the central section 524 of each of those members can be adjusted, the MRI coil device 526 can be positioned precisely very close to the desired portion the patient's head or neck.

Figure 27:
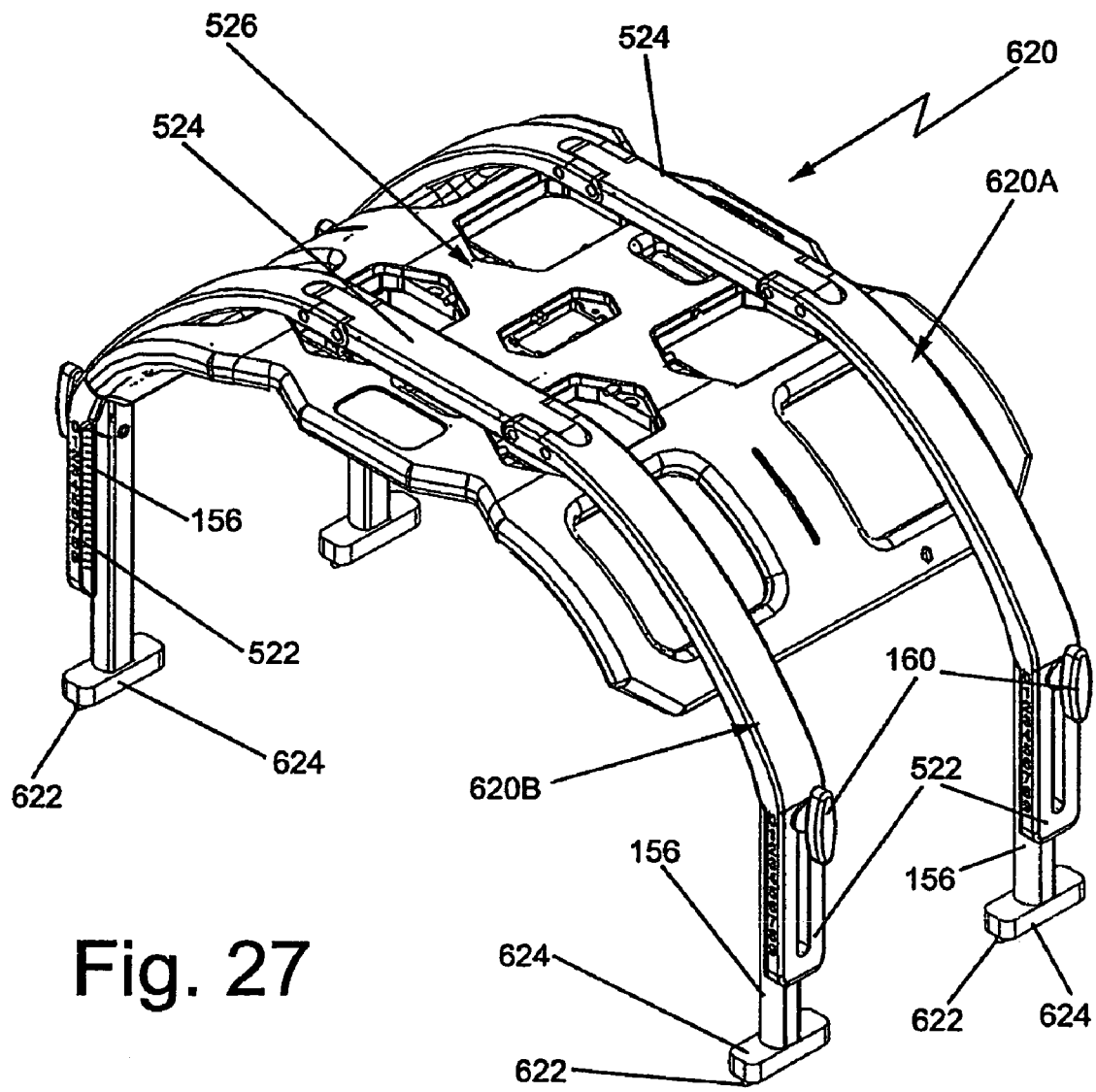
FIG. 27 is a view, similar to FIG. 26, but showing an alternative embodiment of the MRI coil positioning device of this invention.

In FIG. 27 there is shown an alternative embodiment 620 of an MRI coil positioning device. The device 620 is similar in construction to device 520, except that the means for releasably securing it to the patient support panel is different, i.e., it doesn't make use of the clamping mechanisms of the device 520. The reason for that variation is that the device 620 is arranged for use with a patient support panel that is different from the patient support panel 22. In particular, the MRI coil positioning device 620 is arranged to be used with a Siemens couchtop/overlay. That couchtop/overlay includes a plurality of mounting slots extending along the couchtop/overlay adjacent its two longitudinally extending sides. Each of the mounting slots is arranged to receive a respective tab or projection of a positioning member to be releasably secured to the couchtop/overlay. Thus, as will be seen and described hereinafter the MRI coil positioning device 620 makes use of tabs or projections from the side legs of its bridge members.

Figure 27A:
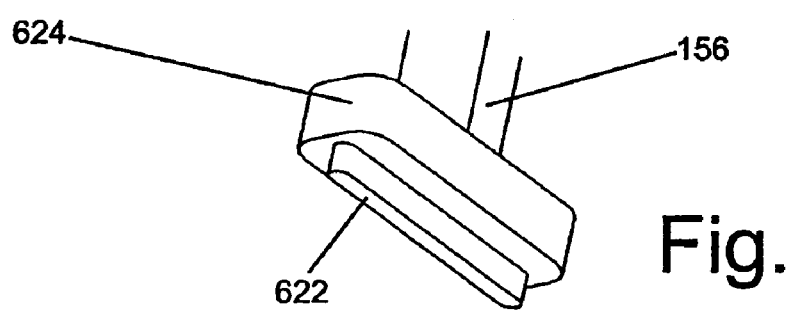
FIG. 27A is an enlarged isometric view of the bottom portion of one of the legs of the MRI coil positioning device shown in FIG. 27.

In the interest of brevity all of the details of the construction and use of the MRI coil positioning device 620 will not be reiterated herein and those features/components of it that are common to the MRI coil positioning device 520 will be given the same reference numbers. Thus, as can be seen in FIG. 27 the device 620 is in the form of a pair of bridge member 620A and 620B, each of which comprises a pair of upstanding side legs 522 and a central section 524 bridging those legs. The MRI coil device 526 is mounted on the central sections 524 of the bridge members 620A and 620B in a similar manner as described with respect to the MRI coil positioning device 520. As best seen in FIG. 27A, the lower end of each of the side legs 522 of each bridge member is in the form of an elongated tab 622 projecting downward from a base block 624. Each projection 622 is shaped and sized to fit within any one of the mounting slots of the couchtop/overlay, with the contiguous portion of the base block engaging the top surface of the couchtop/overlay contiguous with the mounting slot. Accordingly, the bridge members 620A and 620B and the MRI coil device 526 supported thereby can be positioned at any desired position along the couchtop/overlay where there are mounting slots suitable for disposing the MRI coil device adjacent the head or neck of the patient.

It should be pointed out at this juncture that the positioning devices 520 and 620 can, if appropriate and desired, include only a single bridge member in lieu of the pair of bridge members used in those two disclosed embodiments. In fact, this invention contemplates that any number of bridge members can be used to support the MRI coil device, depending upon the size of the MRI coil device.

As should be appreciated from the foregoing many of the various devices of the subject invention can be used to form fit to various regions of a patient's anatomy and create a top layer of a comfortable but controlling patient sandwich in concert with a vacuum pad underneath the patient and positioned and indexed on the SBRT patient support panel. Moreover, the modular design of the subject system provides complete versatility of patient positioning and patient immobilization. Those features and the ability to transport the patient on the patient support panel are keys to having a successful solution and market acceptance. Some or even most of the patient support panel accessories can be "off the shelf" commercial products that mount using standard locking bars, the flexibility with which these designs may be applied to accommodate almost any imaginable combination of methods for performance. Moreover, modular design approach supports complete immobilization of any body part or combination of parts, yet also works well with a minimalist approach. The capability to set up patients outside the treatment room is a significant value for improving work flow efficiency. All of the components of the system of this invention can be produced from a variety of satisfactory materials that are friendly to the radiation and imaging environments.

Without further elaboration the foregoing will so fully illustrate our invention that others may, by applying current or future knowledge, adopt the same for use under various conditions of service.

We claim:

1. A system for positioning a patient on a treatment table for some type of therapy that is to be repeated, wherein the position of at least a portion of the patient's body to be treated is to be held in a predetermined fixed position, said system comprising a patient support panel and at least one positioning component arranged to be releasably mounted on the patient support panel at a desired position thereon to hold the at least one portion of the patient's body at the desired position, said patient support panel comprising a generally planar member having a pair of longitudinally extending integral side rails, each of said side rails having a series of longitudinally spaced indexing apertures, said apertures being aligned in pairs for releasably mounting a first component between any of said pairs at a desired longitudinal position along said patient support panel via a component mounting bar having at least one pin projecting upward therefrom for receipt within the first component, said component mounting bar having a pair of ends, one of said ends being arranged for receipt in one of said apertures in any of said pairs of apertures and the other of said ends being arranged for receipt in the other of said apertures in said pair of apertures, said at least one positioning component comprising a bridge member bridging said panel and including at least one clamp having a mouth to receive a respective one of said side rails therein for direct releasable securement thereto at any longitudinal position therealong.

2. The system of claim 1 wherein said bridge member comprises a pair of legs and a central section bridging said legs, at least one of said legs having said at least one clamp mounted thereon.

3. The system of claim 2 wherein each of said legs is adjustable in height.

4. The system of claim 2 wherein said central section of said bridge member includes an adjustable member arranged to be brought into engagement with the at least one portion of the patient's body.

5. The system of claim 4 additionally comprising a body conforming component disposed on said patient support panel under said adjustable member so that the at least one portion of the patient is held snuggly between said body conforming component and said adjustable member of said at least one positioning component.

6. The system of claim 5 wherein said body conforming component comprises a flexible cushion filled with a multitude of beads to enable it to readily conform to the contour of the at least one portion of the patient's body and thereafter be evacuated of air to fix the shape of that contour so long as the cushion remains evacuated of air.

7. The system of claim 6 wherein said body conforming component extends only a portion of the length of said patient support panel.

8. The system of claim 7 wherein said body conforming component extends approximately the entire length said patient support panel.

9. The system of claim 5 wherein said body conforming component is said first component and comprises a preformed cushion.

10. The system of claim 9 wherein the cushion is shaped to accommodate the underside of the patient's knees.

11. The system of claim 9 wherein said cushion is shaped to accommodate the feet of the patient.

12. The system of claim 11 wherein said cushion includes two cavities, one for each of the patient's feet.

13. The system of claim 9 wherein said cushion includes a pair of apertures therein and wherein said cushion is adapted to be mounted on said patient support table by the upward projecting pins of the component mounting bar.

14. The system of claim 5 wherein said adjustable member comprises a cushion.

15. The system of claim 5 wherein said adjustable member is inflatable.

16. The system of claim 15 wherein said adjustable member comprises a flexible cushion filled with a multitude of beads to enable it to readily conform to the contour of the at least one portion of the patient's body and thereafter be evacuated of air to fix the shape of that contour so long as the cushion remains evacuated of air.

17. The system of claim 1 additionally comprising a pair of handles arranged to be releasably secured to said rails of said patient support panel.

18. The system of claim 17 wherein each of said pair of handles includes a clamp for releasably securing it to an associate rail at any longitudinal position therealong.

19. The system of claim 1 wherein said planar support panel include at least one permanent handle.

20. A device for use on a patient treatment table to enable some type of therapy that is to be repeated to be provided to a patient, wherein the position of at least a portion of the patient's body to be treated is to be held in a predetermined fixed position, said device comprising a frame arranged to be mounted on the treatment table, the frame comprising a pair of longitudinally extending integral side rails, each of said side rails having a series of longitudinally spaced indexing apertures, said apertures being aligned in pairs for releasably mounting a first component between any of said pairs at a desired longitudinal position along the device via a component mounting bar having at least one pin projecting upward therefrom for receipt within the first component, said component mounting bar having a pair of ends, one of said ends being arranged for receipt in one of said apertures in any of said pairs of apertures and the other of said ends being arranged for receipt in the other of said apertures in said pair of apertures, said side rails also being arranged to releasably mount at least one positioning component thereon at any longitudinal position along said side rails by means of at least one clamping member associated with said at least one positioning component, said at least one positioning component comprising a bridge member bridging said panel, said at least one clamping member having a mouth to receive a respective one of said side rails therein for direct releasable securement thereto at any longitudinal position therealong.

* * * * *